US009782123B2

(12) United States Patent
Freeman et al.

(10) Patent No.: US 9,782,123 B2
(45) Date of Patent: Oct. 10, 2017

(54) INTEGRATED RESUSCITATION

(75) Inventors: Gary A. Freeman, Newton Center, MA (US); Mark Totman, Winchester, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 1317 days.

(21) Appl. No.: 11/928,087

(22) Filed: Oct. 30, 2007

(65) Prior Publication Data
US 2008/0046015 A1    Feb. 21, 2008

Related U.S. Application Data

(62) Division of application No. 10/954,633, filed on Sep. 30, 2004, now abandoned.

(51) Int. Cl.
*A61N 1/39* (2006.01)
*A61N 1/04* (2006.01)
(Continued)

(52) U.S. Cl.
CPC .......... *A61B 5/4836* (2013.01); *A61B 5/0245* (2013.01); *A61B 5/02438* (2013.01);
(Continued)

(58) Field of Classification Search
CPC ...... A61N 1/36014; A61N 1/39; A61N 1/046; A61N 1/0472; A61N 1/3968;
(Continued)

(56) References Cited

U.S. PATENT DOCUMENTS 3,513,850 A    5/1970 Weber 3,865,101 A    2/1975 Saper et al.
(Continued)

FOREIGN PATENT DOCUMENTS

GB    9713345.8    6/1997
GB    2314618    1/1998
(Continued)

OTHER PUBLICATIONS

American Red Cross—Adult CPR/AED Training—Workplace Programs, http://www.redcross.org/hss/cpraed.html, printed from Internet May 14, 1999.
(Continued)

*Primary Examiner* — Christopher D Koharski
*Assistant Examiner* — Natasha Patel
(74) *Attorney, Agent, or Firm* — Fish & Richardson P.C.

(57) ABSTRACT

A resuscitation system for use by a rescuer for resuscitating a patient, comprising at least two high-voltage defibrillation electrodes, a first electrical unit comprising circuitry for providing resuscitation prompts to the rescuer, a second electrical unit separate from the first unit and comprising circuitry for providing defibrillation pulses to the electrodes, and circuitry for providing at least one electrical connection between the first and second units. In another aspect, at least two electrical therapy electrodes adapted to be worn by the patient for extended periods of time, circuitry for monitoring the ECG of the patient, an activity sensor adapted to be worn by the patient and capable of providing an output from which the patient's current activity can be estimated, and at least one processor configured for estimating the patient's current activity by analyzing the output of the activity sensor, analyzing the ECG of the patient, and determining whether electrical therapy should be delivered to the electrodes.

20 Claims, 17 Drawing Sheets

(51) Int. Cl.
- *A61B 5/00* (2006.01)
- *A61H 31/00* (2006.01)
- *A61B 5/11* (2006.01)
- *A61B 5/024* (2006.01)
- *A61B 5/0402* (2006.01)
- *A61B 5/1455* (2006.01)
- *A61B 7/02* (2006.01)
- *A61N 1/362* (2006.01)
- *A61B 5/0245* (2006.01)
- *A61B 5/04* (2006.01)

(52) U.S. Cl.
CPC ........ *A61B 5/0402* (2013.01); *A61B 5/04012* (2013.01); *A61B 5/1116* (2013.01); *A61B 5/1118* (2013.01); *A61B 5/14551* (2013.01); *A61B 5/7282* (2013.01); *A61B 7/02* (2013.01); *A61H 31/005* (2013.01); *A61H 31/007* (2013.01); *A61N 1/046* (2013.01); *A61N 1/0492* (2013.01); *A61N 1/3625* (2013.01); *A61N 1/39* (2013.01); *A61N 1/3968* (2013.01); *A61N 1/3987* (2013.01); *A61N 1/3993* (2013.01); *A61H 2031/002* (2013.01); *A61H 2201/5007* (2013.01); *A61H 2201/5043* (2013.01); *A61H 2201/5048* (2013.01); *A61H 2201/5061* (2013.01); *A61H 2201/5084* (2013.01); *A61H 2201/5097* (2013.01); *A61H 2230/04* (2013.01); *A61H 2230/207* (2013.01); *A61N 1/0472* (2013.01)

(58) Field of Classification Search
CPC .. A61N 1/3987; A61N 1/3993; A61B 5/1116; A61B 5/1118; A61B 4/4836; A61B 5/7282; A61H 31/005; A61H 31/007; A61H 2031/002; A61H 2201/5007; A61H 2201/5043; A61H 2201/5048; A61H 2201/5061; A61H 2201/5084; A61H 2201/5097; A61H 2230/04; A61H 2230/207
USPC .................................................. 607/5; 601/41
See application file for complete search history.

(56) References Cited

U.S. PATENT DOCUMENTS

| | | | |
|---|---|---|---|
| 4,019,501 | A | 4/1977 | Harris |
| 4,077,400 | A | 3/1978 | Harrigan |
| 4,088,138 | A | 5/1978 | Diack et al. |
| 4,095,590 | A | 6/1978 | Harrigan |
| 4,193,064 | A | 3/1980 | Snyder |
| 4,198,963 | A | 4/1980 | Barkalow et al. |
| 4,198,964 | A | 4/1980 | Honneffer |
| RE30,372 | E | 8/1980 | Mirowski et al. |
| 4,273,114 | A | 6/1981 | Barkalow et al. |
| 4,326,507 | A | 4/1982 | Barkalow |
| 4,491,423 | A | 1/1985 | Cohen |
| 4,588,383 | A | 5/1986 | Parker et al. |
| 4,610,254 | A | 9/1986 | Morgan et al. |
| 4,619,265 | A | 10/1986 | Morgan et al. |
| 4,757,821 | A | 7/1988 | Snyder |
| 4,797,104 | A | 1/1989 | Laerdal et al. |
| 4,863,385 | A | 9/1989 | Pierce |
| 4,928,674 | A | 5/1990 | Halperin et al. |
| 4,928,690 | A | 5/1990 | Heilman et al. |
| 4,932,879 | A | 6/1990 | Ingenito et al. |
| 4,974,600 | A * | 12/1990 | Reyes ................ A61N 1/39 600/509 |
| 5,081,993 | A | 1/1992 | Kitney et al. |
| 5,193,537 | A | 3/1993 | Freeman |
| 5,241,302 | A | 8/1993 | Thong |
| 5,247,945 | A | 9/1993 | Heinze et al. |
| 5,285,792 | A | 2/1994 | Sjoquist et al. |
| 5,330,526 | A | 7/1994 | Fincke et al. |
| 5,342,404 | A | 8/1994 | Alt et al. |
| 5,348,008 | A | 9/1994 | Bornn et al. |
| RE34,800 | E | 11/1994 | Hutchins |
| 5,391,187 | A | 2/1995 | Freeman |
| 5,409,010 | A | 4/1995 | Beach et al. |
| 5,431,685 | A | 7/1995 | Alt |
| 5,454,779 | A | 10/1995 | Lurie et al. |
| 5,466,244 | A | 11/1995 | Morgan |
| 5,472,453 | A | 12/1995 | Alt et al. |
| 5,474,574 | A | 12/1995 | Payne et al. |
| 5,496,257 | A | 3/1996 | Kelly |
| 5,507,778 | A | 4/1996 | Freeman |
| 5,511,553 | A | 4/1996 | Segalowitz |
| 5,514,079 | A | 5/1996 | Dillon |
| 5,533,958 | A | 7/1996 | Wilk |
| 5,562,710 | A | 10/1996 | Olsen et al. |
| 5,591,213 | A | 1/1997 | Morgan |
| 5,611,815 | A | 3/1997 | Cole et al. |
| 5,617,853 | A | 4/1997 | Morgan |
| 5,619,265 | A | 4/1997 | Suzuki et al. |
| 5,645,522 | A | 7/1997 | Lurie et al. |
| 5,645,571 | A | 7/1997 | Olson et al. |
| 5,662,690 | A | 9/1997 | Cole et al. |
| 5,700,281 | A | 12/1997 | Brewer et al. |
| 5,735,879 | A | 4/1998 | Gliner et al. |
| 5,787,880 | A | 8/1998 | Swanson et al. |
| 5,792,190 | A | 8/1998 | Olson et al. |
| 5,853,292 | A | 12/1998 | Eggert et al. |
| 5,913,685 | A | 6/1999 | Hutchins |
| 5,993,398 | A | 11/1999 | Alperin |
| 6,021,349 | A | 2/2000 | Arand et al. |
| 6,120,442 | A | 9/2000 | Hickey |
| 6,125,299 | A | 9/2000 | Groenke et al. |
| 6,148,233 | A * | 11/2000 | Owen .................. A61N 1/0452 607/5 |
| 6,155,257 | A | 12/2000 | Lurie et al. |
| 6,178,357 | B1 | 1/2001 | Gliner et al. |
| 6,185,458 | B1 | 2/2001 | Ochs et al. |
| 6,193,519 | B1 | 2/2001 | Eggert et al. |
| 6,220,866 | B1 | 4/2001 | Amend et al. |
| 6,224,562 | B1 | 5/2001 | Lurie et al. |
| 6,238,349 | B1 | 5/2001 | Hickey |
| 6,306,107 | B1 | 10/2001 | Myklebust et al. |
| 6,334,070 | B1 | 12/2001 | Nova et al. |
| 6,351,671 | B1 | 2/2002 | Myklebust et al. |
| 6,356,785 | B1 | 3/2002 | Snyder et al. |
| 6,371,765 | B1 | 4/2002 | Wall et al. |
| 6,390,996 | B1 | 5/2002 | Halperin et al. |
| 6,428,323 | B1 | 8/2002 | Pugh |
| 6,443,735 | B1 | 9/2002 | Eggert et al. |
| 6,477,430 | B1 * | 11/2002 | Feuersanger .......... A61N 1/046 607/142 |
| 6,503,087 | B1 | 1/2003 | Eggert et al. |
| 6,546,285 | B1 * | 4/2003 | Owen et al. ...................... 607/5 |
| 6,572,547 | B2 | 6/2003 | Miller et al. |
| 6,575,914 | B2 | 6/2003 | Rock et al. |
| 6,675,051 | B2 * | 1/2004 | Janae .................. A61N 1/046 600/372 |
| 6,752,771 | B2 | 6/2004 | Rothman et al. |
| 6,758,676 | B2 | 7/2004 | Eggert et al. |
| 6,827,695 | B2 | 12/2004 | Palazzolo et al. |
| 6,872,080 | B2 | 3/2005 | Pastrick et al. |
| 6,961,612 | B2 | 11/2005 | Elghazzawi et al. |
| 7,010,344 | B2 * | 3/2006 | Burnes et al. ..................... 607/4 |
| 7,072,712 | B2 * | 7/2006 | Kroll et al. ........................ 607/5 |
| 7,118,542 | B2 | 10/2006 | Palazzolo et al. |
| 7,122,007 | B2 | 10/2006 | Querfurth |
| 7,164,945 | B2 | 1/2007 | Hamilton et al. |
| 7,190,999 | B2 | 3/2007 | Geheb et al. |
| 7,220,235 | B2 | 5/2007 | Geheb et al. |
| 7,310,553 | B2 | 12/2007 | Freeman |
| RE40,471 | E | 8/2008 | Groenke et al. |
| 7,454,244 | B2 | 11/2008 | Kassab et al. |
| 7,706,878 | B2 | 4/2010 | Freeman |
| 7,761,139 | B2 | 7/2010 | Tearney et al. |
| 7,822,470 | B2 | 10/2010 | Osypka et al. |
| 7,837,669 | B2 | 11/2010 | Dann et al. |

(56) References Cited

U.S. PATENT DOCUMENTS

| | | | |
|---|---|---|---|
| 7,846,138 | B2 | 12/2010 | Dann et al. |
| 8,012,135 | B2 | 9/2011 | Dann et al. |
| 2001/0011159 | A1 | 8/2001 | Cantrell et al. |
| 2001/0018562 | A1 | 8/2001 | Sherman et al. |
| 2001/0047140 | A1* | 11/2001 | Freeman .................. 601/41 |
| 2002/0024888 | A1 | 2/2002 | Schreiber |
| 2002/0026131 | A1 | 2/2002 | Halperin |
| 2002/0026229 | A1 | 2/2002 | Weil et al. |
| 2002/0055694 | A1 | 5/2002 | Halperin et al. |
| 2002/0165471 | A1 | 11/2002 | Halperin et al. |
| 2002/0193711 | A1 | 12/2002 | Halperin et al. |
| 2003/0014055 | A1 | 1/2003 | Svadovskiy |
| 2003/0032988 | A1* | 2/2003 | Fincke .................. 607/5 |
| 2003/0055460 | A1 | 3/2003 | Owen et al. |
| 2003/0083699 | A1 | 5/2003 | Hamilton et al. |
| 2003/0158593 | A1 | 8/2003 | Heilman et al. |
| 2003/0192547 | A1 | 10/2003 | Lurie et al. |
| 2004/0039313 | A1 | 2/2004 | Sherman et al. |
| 2004/0039419 | A1* | 2/2004 | Stickney et al. .......... 607/5 |
| 2004/0044374 | A1 | 3/2004 | Weinberg et al. |
| 2004/0049118 | A1 | 3/2004 | Ideker et al. |
| 2004/0058305 | A1 | 3/2004 | Lurie et al. |
| 2004/0162510 | A1 | 8/2004 | Jayne et al. |
| 2004/0162585 | A1 | 8/2004 | Elghazzawi et al. |
| 2004/0162586 | A1 | 8/2004 | Covey et al. |
| 2004/0162587 | A1 | 8/2004 | Hampton et al. |
| 2004/0186525 | A1 | 9/2004 | Burnes et al. |
| 2004/0210171 | A1 | 10/2004 | Palazzolo et al. |
| 2004/0214148 | A1* | 10/2004 | Salvino et al. ............ 434/262 |
| 2004/0230140 | A1 | 11/2004 | Steen |
| 2004/0267325 | A1 | 12/2004 | Geheb et al. |
| 2005/0119706 | A1* | 6/2005 | Ideker et al. ............ 607/5 |
| 2005/0209503 | A1 | 9/2005 | Elliott |
| 2005/0256415 | A1 | 11/2005 | Tan et al. |
| 2005/0261742 | A1 | 11/2005 | Nova et al. |
| 2006/0009809 | A1 | 1/2006 | Marcovecchio et al. |
| 2006/0036292 | A1 | 2/2006 | Smith et al. |
| 2006/0041278 | A1 | 2/2006 | Cohen et al. |
| 2006/0089574 | A1 | 4/2006 | Paradis |
| 2006/0116724 | A1* | 6/2006 | Snyder .................. 607/5 |
| 2006/0173500 | A1 | 8/2006 | Walker et al. |
| 2006/0173501 | A1 | 8/2006 | Stickney et al. |
| 2006/0224053 | A1 | 10/2006 | Black et al. |
| 2006/0257377 | A1 | 11/2006 | Atala et al. |
| 2006/0270952 | A1 | 11/2006 | Freeman et al. |
| 2007/0054254 | A1 | 3/2007 | Cook et al. |
| 2008/0176199 | A1 | 7/2008 | Stickney et al. |
| 2008/0312709 | A1 | 12/2008 | Volpe et al. |
| 2012/0112903 | A1 | 5/2012 | Kaib et al. |
| 2014/0043419 | A1 | 2/2014 | Otsuka et al. |
| 2015/0109125 | A1 | 4/2015 | Kaib et al. |

FOREIGN PATENT DOCUMENTS

| | | |
|---|---|---|
| JP | 2004-222785 | 8/2004 |
| WO | 96/10984 | 4/1996 |
| WO | 98/30282 | 7/1998 |
| WO | WO 98/39061 | 9/1998 |
| WO | 99/24114 | 5/1999 |
| WO | 99/25306 | 5/1999 |
| WO | 99/63926 | 12/1999 |
| WO | 99/65560 | 12/1999 |
| WO | 01/56652 | 8/2001 |
| WO | 01/66182 | 9/2001 |
| WO | 02/15836 | 2/2002 |
| WO | 02/072197 | 9/2002 |
| WO | 03/009895 | 2/2003 |
| WO | 2004/037154 | 5/2004 |
| WO | 2004/054656 | 7/2004 |
| WO | WO 2004/056303 | 7/2004 |
| WO | 2004/073493 | 9/2004 |
| WO | 2004/078259 | 9/2004 |
| WO | 2005/021089 | 3/2005 |

OTHER PUBLICATIONS

Aase et al., "Compression Depth Estimation for CPR Quality Assessment Using DSP on Accelerometer Signals," IEEE Transactions on Biomedical Engineering, vol. 49, No. 3, Mar. 2002.

Force Sensing Resistors—An Overview of the Technology, FSR Integration Guide & Evaluation Parts Catalog with Suggested Electrical Interfaces (no date).

Gruben et al., "System for Mechanical Measurements During Cardiopulmonary Resuscitation in Humans," IEEE Transactions on Biomedical Engineering, vol. 37, No. 2, Feb. 1990.

Heartstream—The Background Behind Our Technology, http://www.heartstream.com/techbk.htm, printed from Internet Jun. 25, 1999.

Flewelling, Nellcor Incorporated, Noninvasive Optical Monitoring, Chap. 88, pp. 1346-1353. CRC Press, Inc ., 1995.

Office Action dated Jun. 28, 2011 from corresponding Japanese Application No. 2005-284315.

Abella et al., Circulation, 2005; 111:428-434.

Crit. Care Med. 2000 vol. 28, No. 11 (Suppl.).

Eftestol et al., Circulation, 2000, Predicting Outcome of Defibrillation by Spectral Characterization and Nonparametric Classification of Ventricular Fibrillation in Patients With Out-of-Hospital Cardiac Arrest.

M.R. Pinsky, Journal of Applied Physiology, vol. 60(2), pp. 604-612, Feb. 1986.

Sato et al., Critical Care Medicine, vol. 25(5), May 1997, pp. 733-736.

Yu et al., Circulation, 2002, Adverse Outcomes of Interrupted Precordial Compression During Automated Defibrillation.

* cited by examiner

INTEGRATED RESUSCITATION

CROSS-REFERENCE TO RELATED APPLICATIONS

This application is a divisional application of and claims priority to U.S. application Ser. No. 10/954,633, filed Sep. 30, 2004 now abandoned.

TECHNICAL FIELD

This invention relates to resuscitation systems incorporating defibrillation therapy and resuscitation prompts.

BACKGROUND OF THE INVENTION

Resuscitation can generally include clearing a patient's airway, assisting the patient's breathing, chest compressions, and defibrillation.

The American Heart Association's Basic Life Support for Health Care Providers textbook provides a flow chart at page 4-14 of Chapter 4 that lists the steps of airway clearing, breathing, and circulation (known as A, B, and C), for situations in which there is no defibrillator readily accessible to the rescuer.

Defibrillation (sometimes known as step D) can be performed with the use of an automatic external defibrillator (AED). Most automatic external defibrillators arc actually semi-automatic external defibrillators (SAED), which require a clinician to press a start button, after which the defibrillator analyzes the patient's condition and provides a shock to the patient if the electrical rhythm is shockable and waits for user intervention before any subsequent shock. Fully automatic external defibrillators, on the other hand, do not wait for user intervention before applying subsequent shocks. As used below, automatic external defibrillators (AED) include semi-automatic external defibrillators (SAED).

Both types of defibrillators typically provide an oral stand clear warning before the application of each shock, and then the clinician is expected to stand clear of the patient and may be required to press a button indicating that the clinician is standing clear of the patient. The controls for automatic external defibrillators are typically located on a resuscitation control box.

AEDs are used typically by trained providers such as physicians, nurses, fire department personnel, and police officers. There might be one or two people at a given facility that has an AED who have been designated for defibrillation resuscitation before an ambulance service arrives. The availability of on-site AEDs along with rescuers trained to operate them is important because if the patient experiences a delay of more than 4 minutes before receiving a defibrillation shock the patient's chance of survival can drop dramatically. Many large cities and rural areas have low survival rates for defibrillation because the ambulance response time is slow, although many suburbs have higher survival rates because of the faster ambulance response time due to lack of traffic and availability of hospitals and advanced life support.

Trained lay providers are a new group of AED operators, but they rarely have opportunities to defibrillate. For example, spouses of heart attack victims may become lay providers, but these lay providers can be easily intimidated by an AED during a medical emergency. Consequently, such lay providers can be reluctant to purchase AEDs, or might tend to wait for an ambulance to arrive rather than use an available AED, out of concern that the lay provider might do something wrong.

There are many different kinds of heart rhythms, some of which are considered shockable and some of them are not. For example, a normal rhythm is considered non-shockable, and there are also many abnormal non-shockable rhythms. There are also some abnormal non-viable non-shockable, which means that the patient cannot remain alive with the rhythm, but yet applying shocks will not help convert the rhythm.

As an example of a non-shockable rhythm, if a patient experiences asystole, the heart will not be beating and application of shocks will be ineffective. Pacing is recommended for asystole, and there are other things that an advanced life support team can do to assist such patient, such as the use of drugs. The job of the first responder is simply to keep the patient alive, through the use of CPR and possibly defibrillation, until an advanced life support team arrives. Bradycardias, during which the heart beats too slowly, are non-shockable and also possibly non-viable. If the patient is unconscious during bradycardia, it can be helpful to perform chest compressions until pacing becomes available. Electro-mechanical dissociation (EMD), in which there is electrical activity in the heart but it is not making the heart muscle contract, is non-shockable and non-viable, and would require CPR as a first response. Idio-ventricular rhythms, in which the normal electrical activity occurs in the ventricles but not the atria, can also be non-shockable and nonviable (usually, abnormal electrical patterns begin in the atria). Idio-ventricular rhythms typically result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles.

The primary examples of shockable rhythms, for which a first responder should perform defibrillation, include ventricular fibrillation, ventricular tachycardia, and ventricular flutter.

After using a defibrillator to apply one or more shocks to a patient who has a shockable electrical rhythm, the patient may nevertheless remain unconscious, in a shockable or non-shockable rhythm. The rescuer may then resort to chest compressions. As long as the patient remains unconscious, the rescuer can alternate between use of the defibrillator (for analyzing the electrical rhythm and possibly applying a shock) and performing cardio-pulmonary resuscitation (CPR).

CPR generally involves a repeating pattern of five or fifteen chest compressions followed by a pause. CPR is generally ineffective against abnormal rhythms, but it does keep some level of blood flow going to the patient's vital organs until an advanced life support team arrives. It is difficult to perform CPR over an extended period of time. Certain studies have shown that over a course of minutes, rescuers tend to perform chest compressions with less-than-sufficient strength to cause an adequate supply of blood to flow to the brain. CPR prompting devices can assist a rescuer by prompting each chest compression and breath.

PCI Patent Publication No. WO 99/24114, filed by Heartstream, Inc., discloses an external defibrillator having PCR and ACLS (advanced cardiac life support) prompts.

SUMMARY OF THE INVENTION

In a first aspect, the invention features a resuscitation system for use by a rescuer for resuscitating a patient, comprising at least two high-voltage defibrillation electrodes, a first electrical unit comprising circuitry for providing resuscitation prompts to the rescuer, a second electrical unit separate from the first unit and comprising circuitry for providing defibrillation pulses to the electrodes, and circuitry for providing at least one electrical connection between the first and second units.

Preferred implementations of this aspect of the invention may incorporate one or more of the following. The two electrodes and the first unit may be built into a defibrillation electrode pad assembly. The defibrillation electrodes may be detachable from the defibrillation electrode pad assembly. The first unit may be separate from the two electrodes, and may be connected to the two electrodes by one or more cables. The first unit may be capable of functioning and providing the resuscitation prompts without being electrically connected to the second unit. The first unit may comprise a source of electrical power and a processor. The first unit may have circuitry for monitoring at least one physiological parameter of the patient. The parameter may be an ECG signal. The resuscitation prompts may comprise CPR prompts. The circuitry for providing at least one electrical connection between the first and second units may comprise at least one cable. The circuitry for providing at least one electrical connection between the first and second units may comprise at least one wireless connection. The second unit may be connected directly to the defibrillation electrodes by one or more cables that carry the defibrillation pulses to the electrodes. The circuitry for providing at least one electrical connection between the first and second units may comprise at least one cable for delivering the defibrillation pulses to the first unit, from where they are delivered to the electrodes. The ECG signal may be detected using the defibrillation electrodes. The first unit may comprise a speaker for providing the resuscitation prompts. The resuscitation prompts may comprise spoken and visual prompts. The first unit may comprise a microphone and circuitry for storing sounds recorded during use of the unit. The defibrillation electrodes may be built into an electrode pad assembly and a handle for providing an upward lifting force on the assembly may be provided. The handle may comprise a flexible sheet material. The handle may comprise a substantially rigid material.

In a second aspect, the invention features a resuscitation system for resuscitating a patient, comprising at least two electrical therapy electrodes adapted to be worn by the patient for extended periods of time, circuitry for monitoring the ECG of the patient, an activity sensor adapted to be worn by the patient and capable of providing an output from which the patient's current activity can be estimated, and at least one processor configured for estimating the patient's current activity by analyzing the output of the activity sensor, analyzing the ECG of the patient, and determining whether electrical therapy should be delivered to the electrodes.

Preferred implementations of this aspect of the invention may incorporate one or more of the following. The processor may be configured for estimating whether the patient is moving. The activity sensor may comprise an accelerometer, and the processor may be configured for integrating the output of the accelerometer to provide an estimate of velocity and/or displacement. The processor may be configured to process the output of the activity sensor and use the result of the processing to modify at least one threshold in a technique used for determining a physiological status of patient. The physiological status may comprise determining a risk of impending heart attack or cardiac arrest. The resuscitation system may include a speaker for issuing spoken prompts to the patient, and the processor may decide on the nature of the spoken prompt based on the estimated current activity of the patient. The patient's current activity may comprise estimating the orientation of the patient. Estimating the orientation of the patient may comprise determining whether the patient lying on his back. The electrodes may be defibrillation electrodes and the electrical therapy may comprise a defibrillation pulse. The invention may further comprise an activity sensor adapted to be worn by the patient and capable of providing an output from which the patient's current activity can be estimated, and at least one processor configured for estimating the patient's current activity by analyzing the output of the activity sensor. The at least one processor may be located in the first unit. At least some of the resuscitation prompts delivered by the first unit may be dependent on the estimated current activity of the patient. The current activity may comprise whether the patient is lying on his back, and at least one resuscitation prompt issued when the patient is not on his back may be an instruction to roll the patient on their back prior to beginning CPR.

In a third aspect, the invention features a resuscitation system for resuscitating a patient, comprising at least two electrical therapy electrodes adapted to be worn by the patient for extended periods of time, circuitry for monitoring the ECG of the patient, an activity sensor adapted to be worn by the patient and capable of providing an output from which the patient's current activity can be estimated, and at least one processor configured for estimating the patient's current activity by analyzing the output of the activity sensor, analyzing the ECG of the patient, and determining whether the patient has an elevated probability of cardiac arrest.

Preferred implementations of this aspect of the invention may incorporate one or more of the following. The processor may be configured for determining whether the patient's current activity includes increased physical activity. The processor may be configured for determining an activity level parameter representative of the patient's activity level. The decision of an elevated probability of cardiac arrest may be based on the activity level parameter and a parameter may be derived from the patient's ECG. The decision of an elevated probability of cardiac arrest may be based on the activity level parameter and a measurement of blood pressure. The invention may further comprise the capability of delivering at least one test pulse through the electrodes at a time based, at least in part, on an estimate of the patient's current activity, wherein the test pulse is of a type configured to produce a ventricular premature beat (VPB). The time based on an estimate of the patient's current activity may be shortly after waking in the morning. Prior to delivering the test pulse, the system may issue a prompt to the patient requesting administration of the test pulse and the system may wait for the patient to indicate his consent to administration of the test pulse.

Among the many advantages of the invention (some of which may be achieved only in some of its various aspects and implementations) are that the invention may permit wider distribution and availability of the first unit, which provides resuscitation prompting, than of the second unit, which provides defibrillation therapy. The first unit's relatively lower cost may make it possible for the first unit to be more widely distributed than the second unit. Wider distribution of the first unit may mean more successful rescues, as a patient can be stabilized and prepared for defibrillation using the first unit.

The unit may be worn on a continuous basis by a person at higher risk of a heart attack such as someone who has recently undergone bypass surgery or one who has experienced a myocardial infarction. The early warning of a heightened risk of an impending cardiac arrest provided by the device will allow the wearer of the device to phone a physician or emergency service in advance of the actual cardiac arrest, thus reducing fatality rates of cardiac arrest by early prevention and treatment of the underlying physiological abnormalities rather than treating the consequences of the arrest. The activity sensor provides a means of determining whether or not the wearer of the device is awake or not, thereby providing an accurate way of providing voice prompts and physiological tests in synchrony with the wearer's daily schedule in a non-interfering manner. When used in conjunction with a communication link to medical providers such as an EMS system, the activity sensor also provides a means of determining the state of the victim, whether the victim is vertical or horizontal, and moving, thus potentially lowering false alarm rates and accuracy of diagnosis. The activity sensor may also be used to adjust the thresholds used for various alarms and heart attack risk detection methods. The wearer can activate a keying input on the device indicating chest pain, and in conjunction with the additional ECG, and activity sensor data, the device can more reliably calculate relative risk of impending heart attack or cardiac arrest and with a communication means, potentially contact emergency services directly without intervention of the wearer.

Other features and advantages of the invention will be found in the detailed description, drawings, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
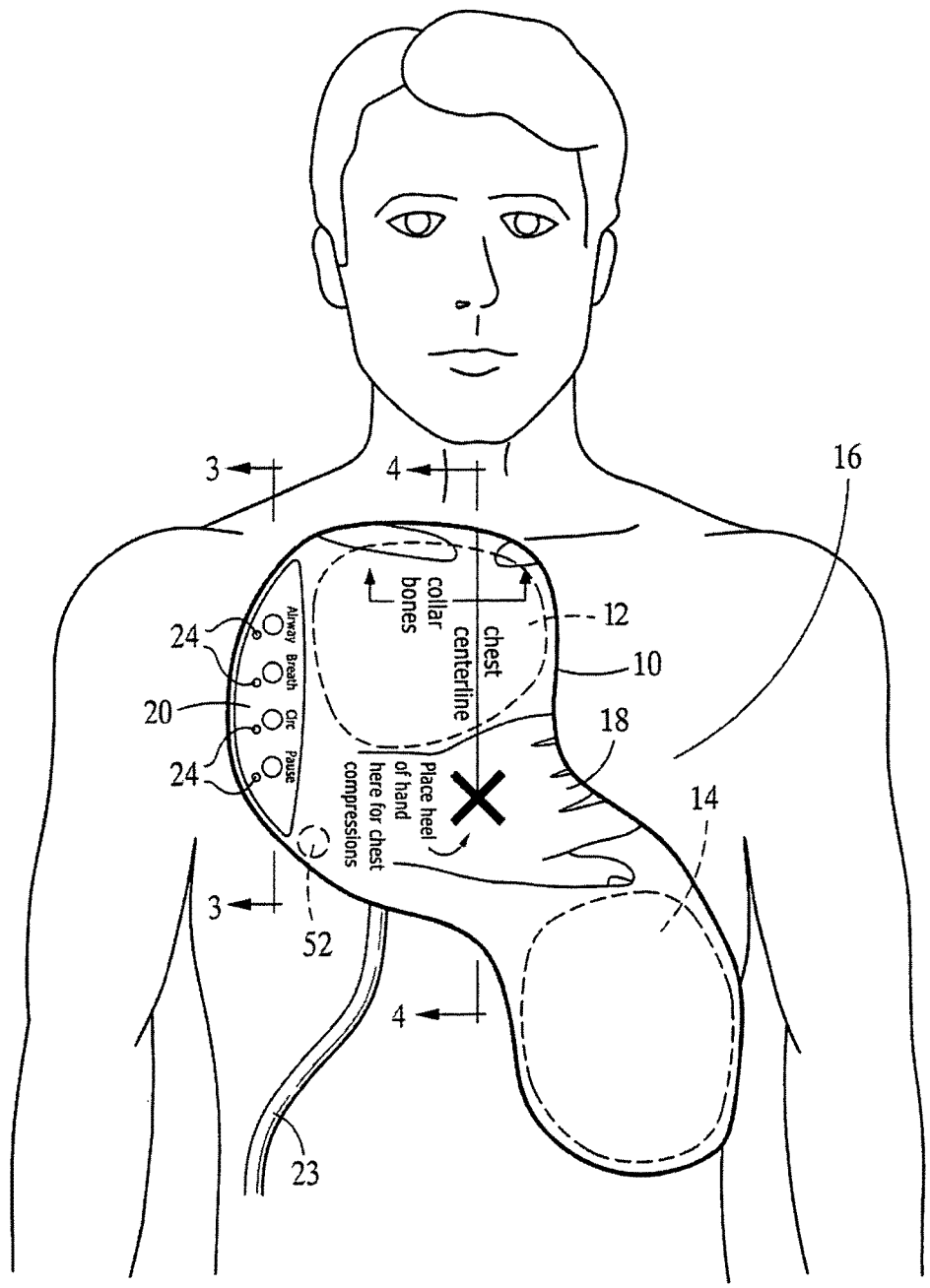
FIG. 1 is a drawing of a defibrillation electrode pad according to the invention, positioned over the chest of a patient.

With reference to FIG. 1, a defibrillation electrode pad 10, which includes high-voltage apex defibrillation electrode 12 and high-voltage sternum defibrillation electrode 14, is placed on the patient's chest 16 and includes a region 18 on which a user may press to perform CPR. Legends on pad 10 indicate proper placement of the pad with respect to the patient's collarbones and the chest centerline and the proper placement of the heel of the rescuer's hand.

A low-profile button panel 20 is provided on the electrode assembly. Button panel 20 has buttons 22, including buttons A (Airway Help), B (Breathing Help), C (Circulation Help) and PAUSE, and may also include adjacent light emitting diodes (LEDs) 24 that indicate which button has been most recently pressed. Button panel 20 is connected by a cable 23 to a remote resuscitation control box 26, shown in FIG. 2. Button panel 20 provides rigid support underneath buttons A, B, C, and PAUSE against which the switches can be pushed in order to ensure good switch closure while the electrode rests on a patient. Button panel 20 includes components that make electrical contact with silver/silver-chloride electrical circuit components screen-printed on a polyester base of defibrillation electrode pad 10, as is described in detail below.

A pulse detection system based on shining light through the patient's vascular bed, e.g., a pulse oximetry system 52, is incorporated into defibrillation electrode pad 10. Pulse oximetry system 52 includes a red light-emitting diode, a near-infrared light-emitting diode, and a photodetector diode (see FIG. 5) incorporated into defibrillation electrode pad 10 in a manner so as to contact the surface of the patient's chest 16. The red and near-infrared light-emitting diodes emit light at two different wavelengths, which is diffusely scattered through the patient's tissue and detected by the photodetector diode. The information obtained from the photodetector diode can be used to determine whether the patient's blood is oxygenated, according to known noninvasive optical monitoring techniques.

In another implementation, the pulse detection system is a phonocardiogram system for listening to the sound of the victim's heart, rather than a pulse oximetry system. The phonocardiogram system includes a microphone and an amplifier incorporated within the electrode pad. Because a heart sound can be confused with microphone noise, the signal processing that must be performed by the microprocessor inside the control box will be more difficult in connection with a phonocardiogram system than in connection with a pulse oximetry system. Nevertheless, there are programs available that can enable the microprocessor to determine whether an ECG signal is present as opposed to microphone noise.

Pulse oximetry is a well-developed, established technology, but it requires good contact between the light sources and the victim's skin so that light can shine down into the victim's vascular bed. Many victims have lots of chest hair, which can interfere with good contact. It may be desirable for different types of electrode pads to be available at a given location (one having a pulse oximetry system and one having a phonocardiogram system) so that a rescuer can select an appropriate electrode pad depending on the nature of the victim.

In another implementation, instead of providing a low-profile button panel, a button housing can be provided that is affixed to an edge of the defibrillation electrode. The housing may be in the form of a clamshell formed of single molded plastic element having a hinge at an edge of the clamshell around which the plastic bends. The two halves of the clamshell can be snapped together around the electrode assembly.

The resuscitation control box (FIG. 2) includes an internal charge storage capacitor and associated circuitry including a microprocessor, an farther includes off/on dial 28, and a "READY" button 30 that the rescuer presses immediately prior to application of a defibrillation shock in order to ensure that the rescuer is not in physical contact with the patient. The microprocessor may be a RISC processor such as a Hitachi SH-3, which can interface well with displays and keyboards, or more generally a processor capable of handling DSP-type (digital signal processing) operations.

The resuscitation control box has printed instructions 32 on its front face listing the basic steps A, B, and C for resuscitating a patient and giving basic instructions for positioning the defibrillation electrode pad on the patient. A speaker 32 orally prompts the user to perform various steps, as is described in detail below.

For example, the resuscitation control box instructs the user, by audible instructions and also through a display 34 on the resuscitation control box, to check the patient's airway and perform mouth-to-mouth resuscitation, and if the patient's airway is still blocked, to press the A (Airway Help) button on the button panel (FIG. 1), upon which the resuscitation control box gives detailed prompts for clearing the patient's airway. If the patient's airway is clear and the patient has a pulse but the patient does not breathe after initial mouth-to-mouth resuscitation, the resuscitation control box instructs the user press the B (Breathing Help) button, upon which the resuscitation control box gives detailed mouth-to-mouth resuscitation prompts. If, during the detailed mouth-to-mouth resuscitation procedure, the rescuer checks the patient's pulse and discovers that the patient has no pulse, the resuscitation control box instructs the user to press the C (Circulation Help) button.

During the circulation procedure, the resuscitation control box receives electrical signals from the defibrillation electrodes and determines whether defibrillation or CPR should be performed. If the resuscitation control box determines that defibrillation is desirable, the resuscitation control box instructs the user to press the "ready" button on the resuscitation control box and to stand clear of the patient. After a short pause, the resuscitation control box causes a defibrillation pulse to be applied between the electrodes. If at any point the resuscitation control box determines, based on the electrical signals received from the electrodes, that CPR is desirable, it will instruct the user to perform CPR.

Thus, the key controls for the system are on the electrodes attached to the patient rather than the resuscitation control box. This is important because it enables the rescuer to remain focused on the patient rather than the control box. The resuscitation control box gets its information directly from the electrodes and the controls on the electrodes.

The resuscitation control box can sense electrical signals from the patient's body during pauses between CPR compressions. Also, as is described below, a compression-sensing element such as an accelerometer or a force-sensing element is provided in the region of the defibrillation electrode pad on which the user presses to perform CPR. The purpose of the compression-sensing or force-sensing element is to allow the resuscitation control box to prompt the user to apply additional compression or force, or to prompt the user to cease CPR if the user is performing CPR at an inappropriate point in time.

Figure 4:
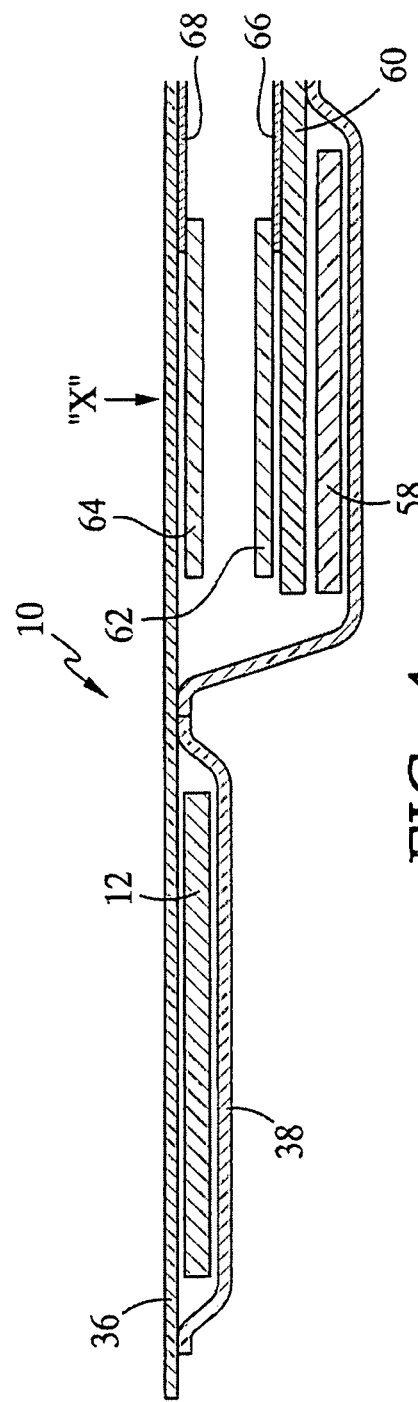
FIG. 4 is a cross-sectional drawing of the defibrillation pad of FIG. 1 taken along line 4-4.

Referring to FIG. 4, in one implementation, each electrode 12, 14 (only electrode 12 is shown) of defibrillation electrode pad 10 includes a polymer-based ink containing a silver/silver-chloride suspension, which is screen-printed on a polyester or plastic base 36. The ink is used to carry the defibrillation current. The screen-printing process first involves applying a resist layer to the polyester base 36. The resist layer is basically a loose mesh of nylon or the like, in which the holes have been filled in at some locations in the mesh. Then, the silver/silver-chloride ink is applied as a paste through the resist layer in a squeegee-like manner. The ink squeezes through the screen and becomes a solid layer. The ink may then be cured or dried. The silver/silver-chloride ink provides good conductivity and good monitoring capabilities.

Thus, the ink can be applied as pattern, as opposed to a solid sheet covering the entire polyester base. For example, U.S. Pat. No. 5,330,526 describes an electrode in which the conductive portion has a scalloped or daisy shape that increases the circumference of the conductive portion and reduces burning of the patient. A conductive adhesive gel 38 covers the exposed surface of each electrode.

In addition, electrical circuit components are also be screen printed on the base, in the same manner as flat circuit components of membrane-covered, laminated panel controls.

Figure 3:
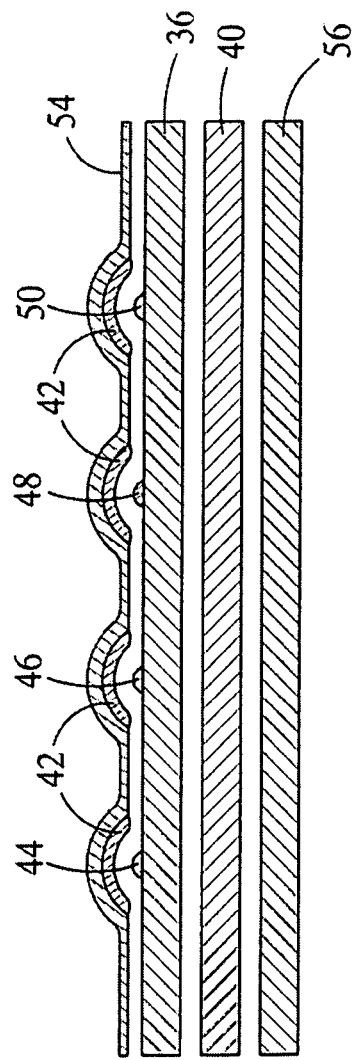
FIG. 3 is a cross-sectional drawing of the defibrillation electrode pad of FIG. 1 taken along line 3-3.

Referring to FIG. 3, a rigid piece 40 of hard plastic, such as PVC or polycarbonate, is laminated beneath substrate 36 and supports buttons A, B, C, and PAUSE. The rigid plastic piece 40 is glued onto substrate 36. Buttons A, B, C, and PAUSE consist of small metal dome snap-action switches that make contact between an upper conductive ink trace 42 and lower conductive ink traces 44, 46, 48, and 50. Buttons A, B, C, and PAUSE serve as controls that can be activated by the user that are physically located either on or immediately adjacent to the electrode assembly itself. Each of buttons A, B, C, and PAUSE may be associated with an adjacent light-emitting diode (LED). For example, LEDs may be glued, using conductive epoxy, onto silver/silver-chloride traces on substrate 36. An embossed polyester laminate layer 54 covers conductive ink trace 42 of buttons A, B, C, and PAUSE, and a foam layer 56 is laminated beneath rigid plastic piece 40.

Referring again to FIG. 4, defibrillation electrode pad 10 includes an extension piece that is placed directly over the location on the patient's body where the rescuer performs chest compressions. This extension piece includes substrate 36, and a semi-rigid plastic supporting member 58 laminated underneath substrate 36 that covers the chest compression area. Semi-rigid supporting member 58 provides somewhat less rigidity than rigid plastic piece 409 provided at the location of buttons A, B, C, and PAUSE (illustrated in FIG. 3).

In implementations having a force-sensing element, a polyester laminate 60, and a force-sensing resistor having two layers of carbon-plated material 62 and 64, are laminated between polyester substrate 36 and semi-rigid supporting member 58. A suitable construction of the force-sensing resistor is illustrated in the FSR Integration Guide & Evaluation Parts Catalog with Suggested Electrical Interfaces, from interlink Electronics. The electrical contact between the two carbon-plated layers of material increases with increased pressure, and the layers of force-sensing resistive material can provide a generally linear relationship between resistance and force. Conductive ink traces 66 and 68 provide electrical connections to the two layers of the force-sensing resistor.

During chest compressions, the rescuer's hands are placed over the extension piece, and the force-sensing resistor of the extension piece is used to sense the force and the timing of the chest compressions. The force-sensing resistor provides information to the resuscitation control box so that the resuscitation control box can provide the rescuer with feedback if the rescuer is applying insufficient force. The resuscitation control box also provides coaching as to the rate at which CPR is performed. In certain situations, the resuscitation control box indicates to the rescuer that CPR should be halted because it is being performed at an inappropriate time, such as immediately prior to application of a defibrillation shock when the rescuer's hands should not be touching the patient, in which case the resuscitation control box will also indicate that the rescuer should stay clear of the patient because the patient is going to experience a defibrillation shock.

As is noted above, during CPR the rescuer pushes on the patient's chest through the extension piece in the vicinity of the electrodes. If the resuscitation control box were to perform analysis during the chest compressions, the chest compressions would be likely to affect the sensed electrical rhythm. Instead, during the pauses between sets of compressions (for example, the pause after every fifth chest compression), the resuscitation control box can perform an electrocardiogram (ECG) analysis. The resuscitation control box might discover, for example, that the patient who is undergoing CPR is experiencing a non-shockable rhythm such as bradycardia, in which case the CPR is required in order to keep the patient alive, but then the resuscitation control box may discover that the rhythm has changed to ventricular fibrillation in the midst of CPR, in which case the resuscitation control box would instruct the rescuer to stop performing CPR so as to allow the resuscitation control box to perform more analysis and possibly apply one or more shocks to the patient. Thus, the rescuer is integrated into a sophisticated scheme that allows complex combinations of therapy.

In another implementation, a compression-sensing element such as an accelerometer may be used in place of a force-sensing element. The accelerometer, such as a solid-state ADXL202 accelerometer, is positioned at the location where the rescuer performs chest compressions. In this implementation, the microprocessor obtains acceleration readings from the accelerometer at fixed time intervals such as one-millisecond intervals, and the microprocessor integrates the acceleration readings to provide a measurement of chest compression. The use of an accelerometer is based on the discovery that it is more important to measure how deeply the rescuer is compressing the chest than to measure how hard the rescuer is pressing. In fact, every victim's chest will have a different compliance, and it is important that the chest be compressed about an inch and a half to two inches in a normal sized adult regardless of the victim's chest compliance.

Figure 2:
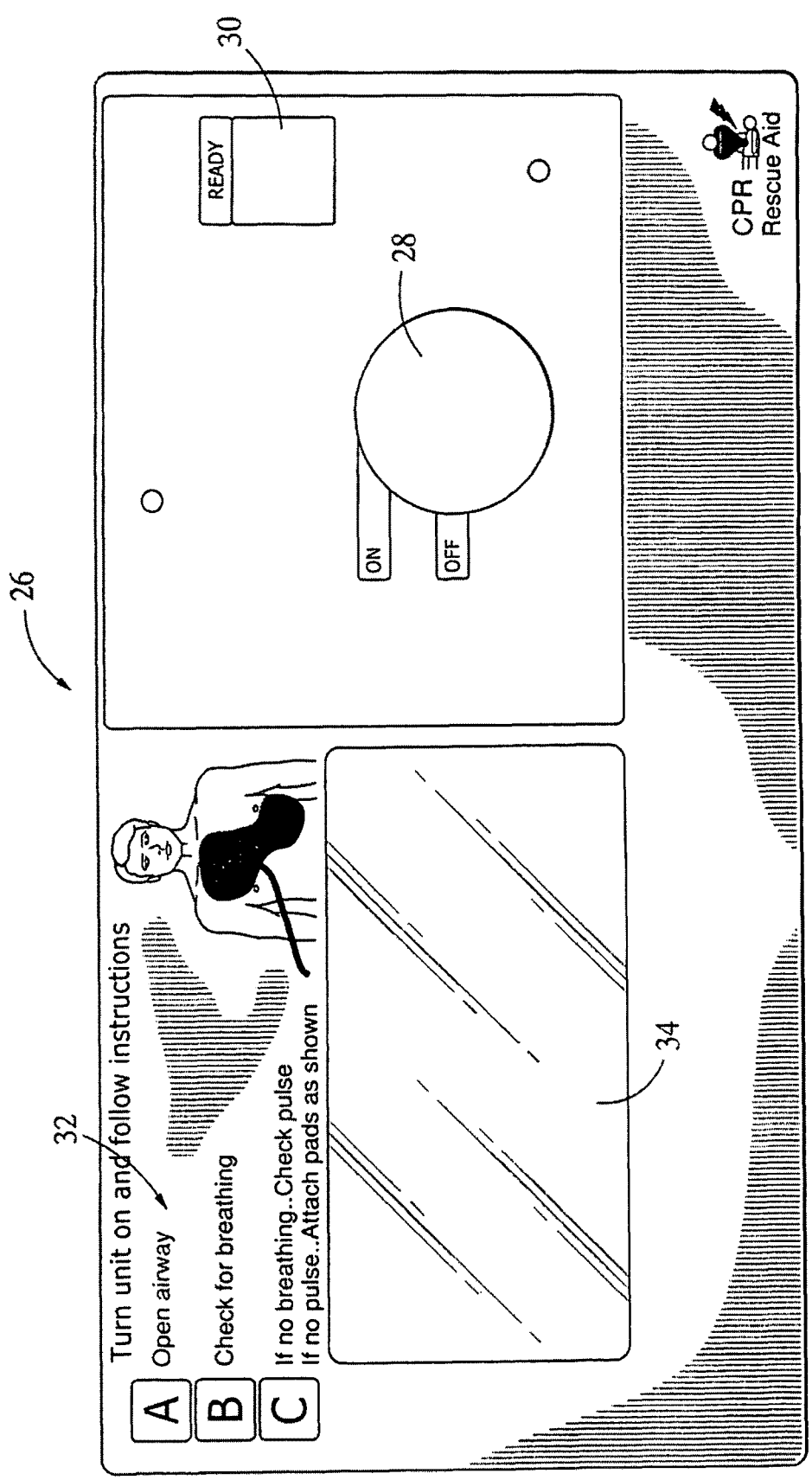
FIG. 2 is a view of the front display panel of a resuscitation control box according to the invention that houses electronic circuitry and provides audible and visual prompting.
Figure 5:
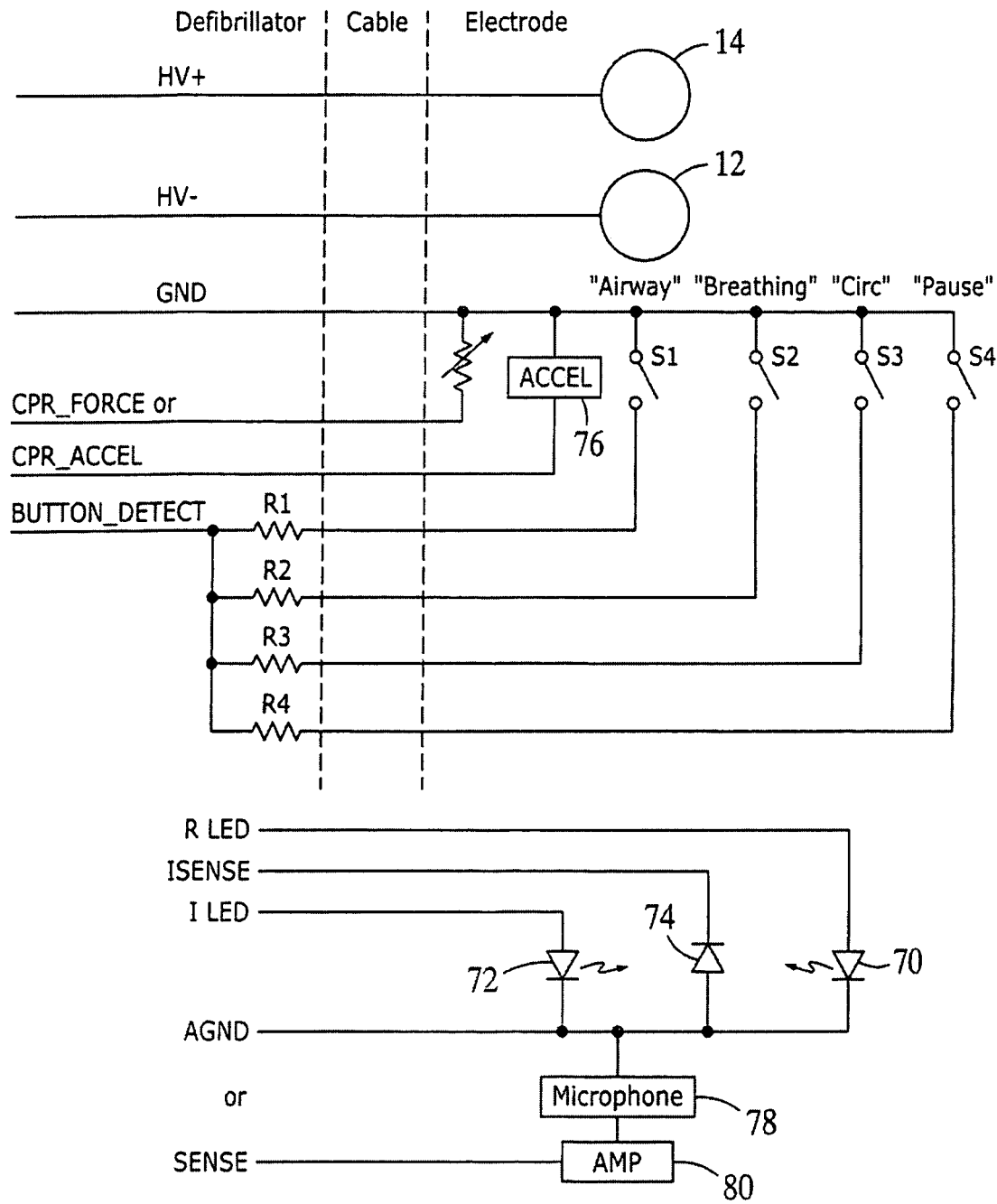
FIG. 5 is a circuit diagram illustrating the circuit interconnections between the defibrillation electrode pad of FIG. 1 and the resuscitation control box of FIG. 2.
Figure 6A:
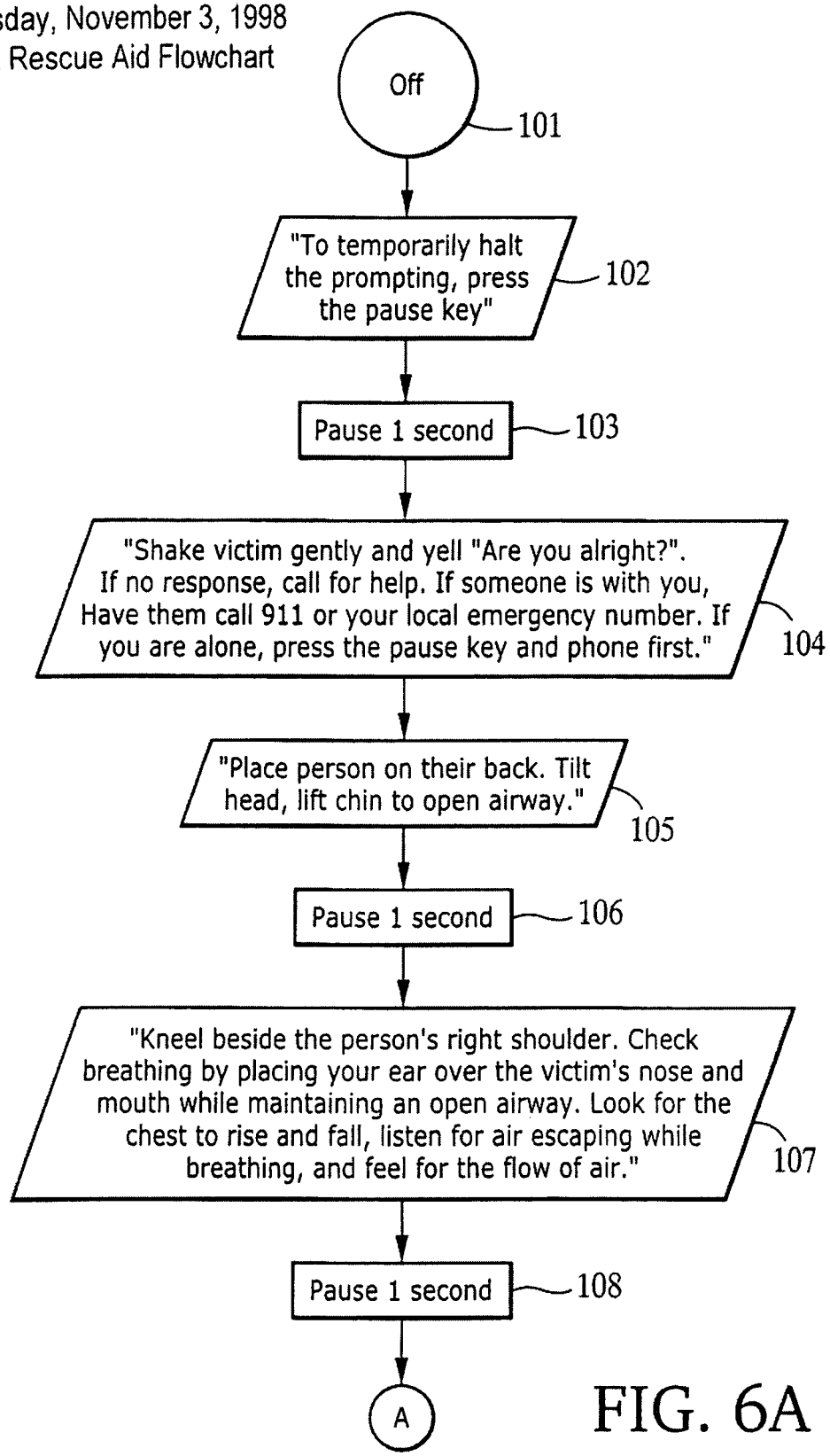
FIGS. 6A and 6B are a flowchart illustrating the initial routine of a resuscitation system according to the invention.
Figure 6B:
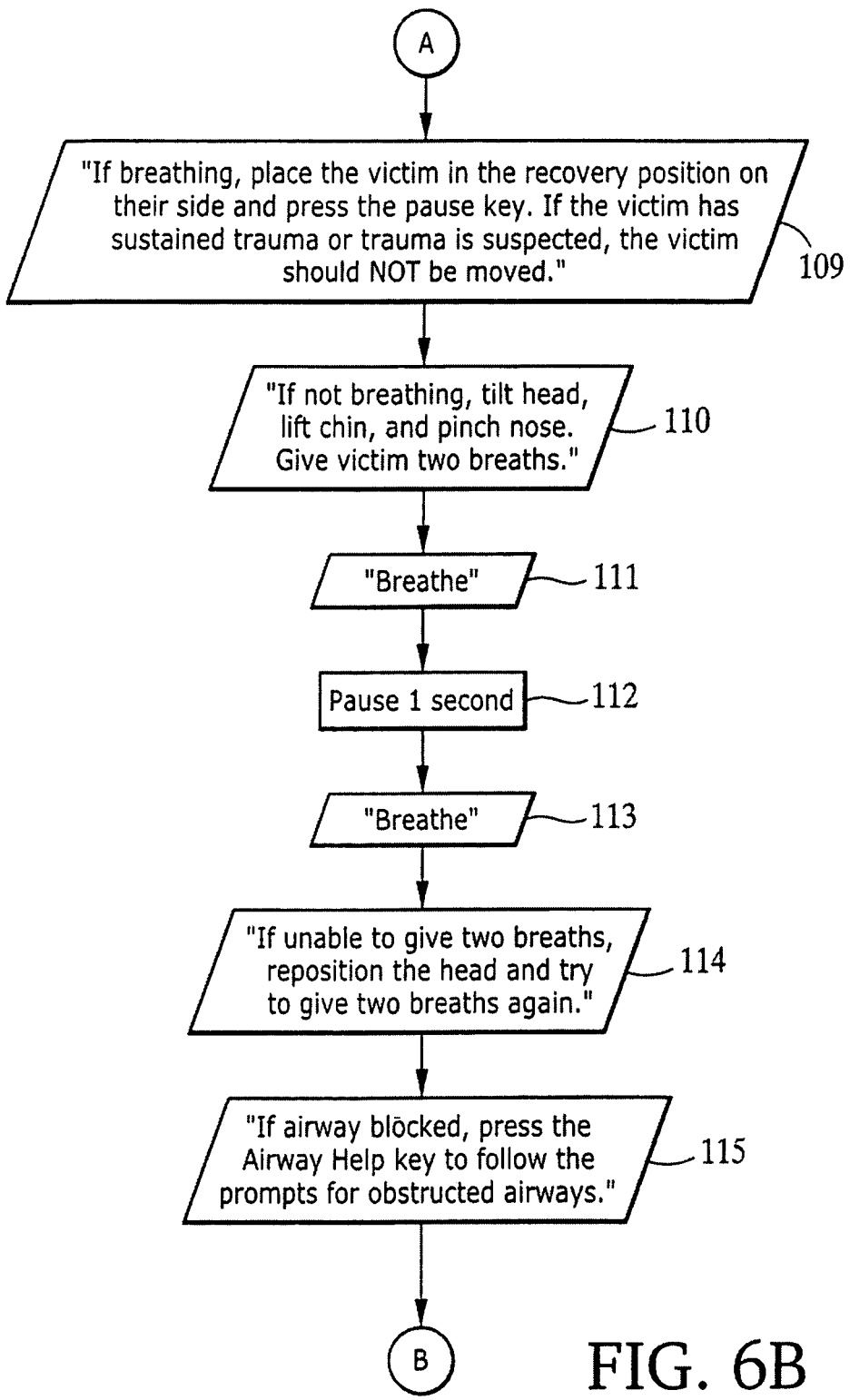
Figure 7A:
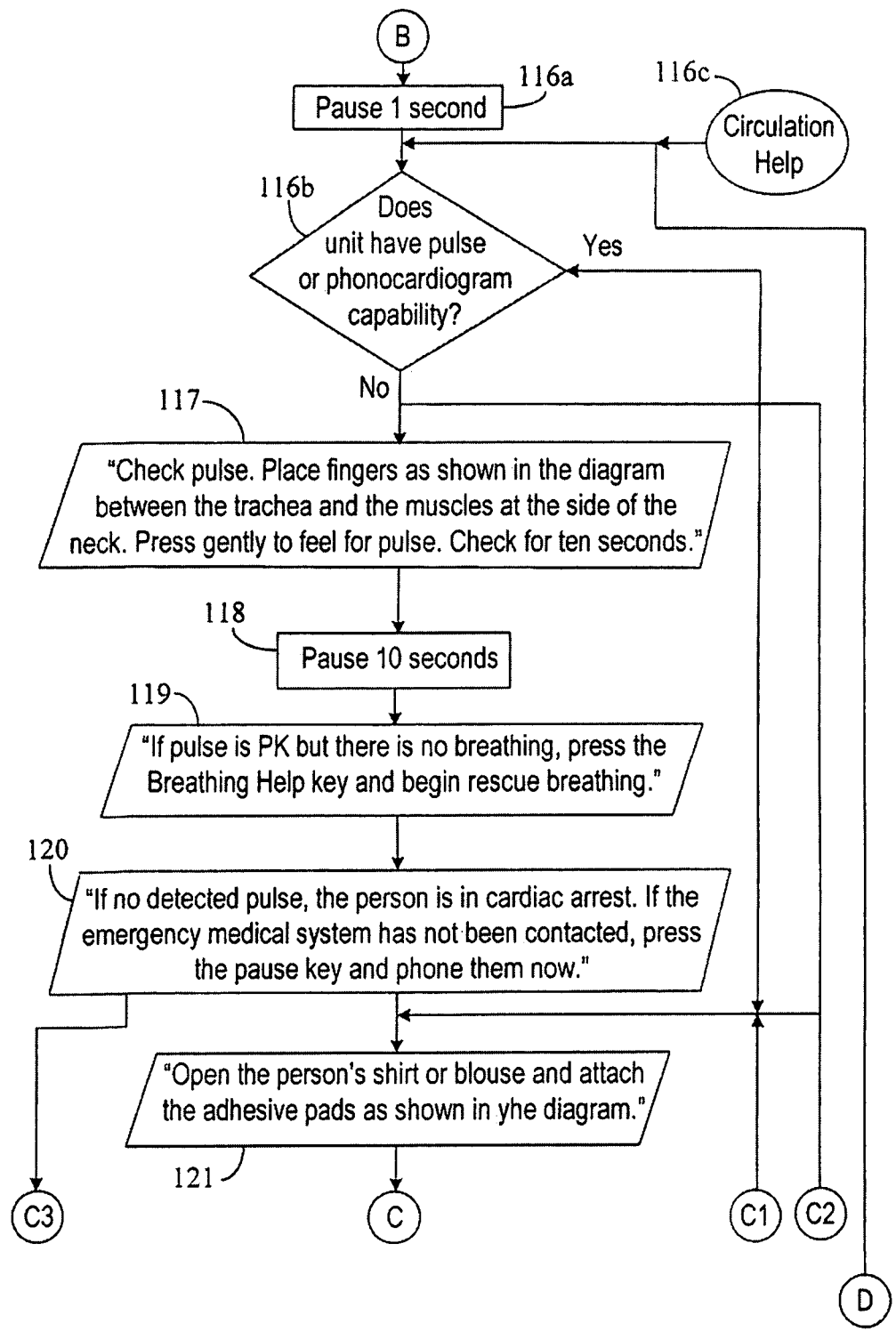
FIGS. 7A, 7B, and 7C are a flowchart illustrating the "circulation help" routine of the resuscitation system.
Figure 7B:
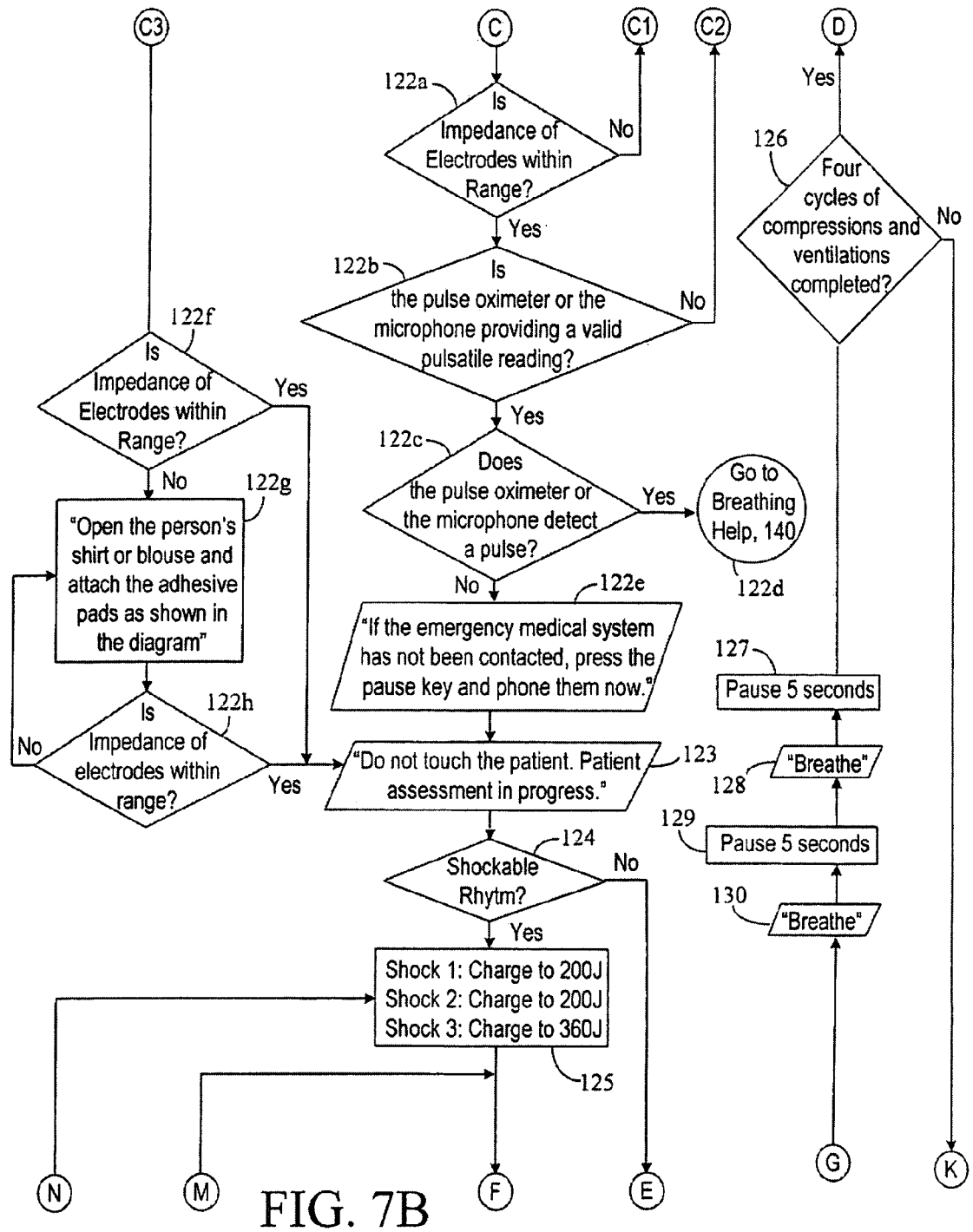
Figure 7C:
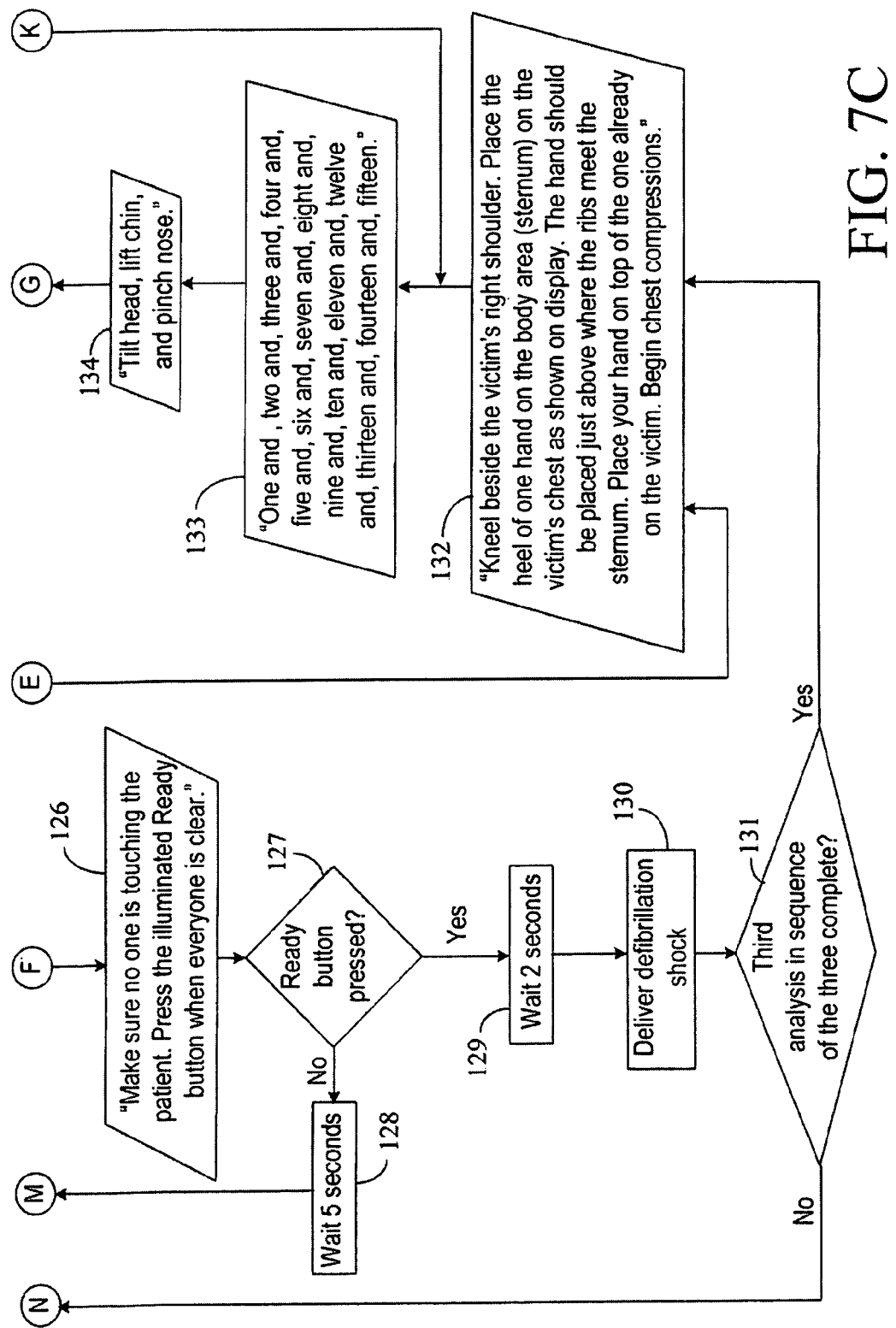

FIG. 5 is a circuit diagram illustrating the circuit interconnections between the defibrillation electrode pad of FIG. 1 through the cable to the resuscitation control box of FIG. 2. Sternum electrode 14 is connected to HV+ at the resuscitation control box, and apex electrode 12 is connected to HV−. A ground GND is connected to the upper conductive ink trace of buttons A, B, C, and PAUSE and to one of the layers of the force-sensing resistor. The other layer of the force-sensing resistor is connected to CPR_FORCE, and the lower conductive ink traces associated with buttons A, B, C, and PAUSE are connected to BUTTON_DETECT through resistors R1, R2, R3, and R4. As an alternative to the use of a force-sensing resistor, a compression-sensing accelerometer 76 may be employed, in which case CPR_FORCE is replaced by CPR_ACCEL connected to accelerometer 76. Red light-emitting diode 70, near-infrared light-emitting diode 72, and photodetector diode 74 of the pulse oximetry system are connected to RLED, ILED, and ISENSE respectively, as well as ground AGND. As an alternative to the use of a pulse oximetry system, a phonocardiogram system may be employed, in which case RLED, ILED, and ISENSE is replaced by SENSE connected to microphone 78 and amplifier 80.

FIGS. 6-9 illustrate the routine of the resuscitation system, which is based on steps A, B, and C (airway, breathing, and circulation). Because step C includes defibrillation as well as chest compressions, all of the aspects of resuscitation are tied together in one protocol (actually, if defibrillation were considered to be a step D distinct from step C, the sequence of steps would be A, B, D, C).

The first thing the rescuer must do upon arriving at the patient is to determine whether the patient is unconscious and breathing. The rescuer opens the patient's airway, administers breaths to the patient if the patient is not breathing, and checks to determine whether a pulse is present. If there is no pulse, rather than perform chest compressions as in standard CPR, the rescuer allows the resuscitation control box to analyze the patient's electrical rhythm, and if the resuscitation control box determines that the rhythm is shockable, the resuscitation control box causes one or more shocks to be applied to the patient, and then the rescuer performs chest compressions. Thus, there is provided a first response system that can keep the patient viable until an advanced life support time arrives to perform advanced techniques including pacing, further defibrillation, and drug therapy.

If the resuscitation control box determines that it should apply one or more defibrillation shocks to the patient, it is important that the rescuer not be anywhere near the patient when the shocks are applied to the patient. Prior to application of each shock, the resuscitation control box instructs the rescuer to please press the "ready" button when everybody is clear of the patient. The pressing of the "ready" button verifies that the rescuer's hands are off of the patient.

When the resuscitation control box detects a shockable rhythm, the resuscitation control box provides shocks of appropriate duration and energy (such as a sequence of shocks of increasing energy from 200 Joules to 300 Joules to the highest setting, 360 Joules, with the resuscitation control box performing analysis after each shock to determine whether another shock is required). If the defibrillation therapy is successful, the patient's rhythm is typically converted from ventricular fibrillation, ventricular tachycardia, or ventricular flutter to bradycardia, idio-ventricular rhythm, or asystole, all of which require CPR. It is rare to convert to a normal rhythm. Once the resuscitation control box has caused defibrillation shocks to be applied to the patient, the resuscitation control box automatically senses the patient's condition, and depending on the patient's condition will either prompt the responder to perform CPR or will not prompt the respond to perform CPR.

Defibrillation equipment can be somewhat intimidating to rescuers who are not medical professionals because the equipment can lead the rescuer to feel responsibility for having to save a loved one's life. It is important that the defibrillation equipment reduce this sense of responsibility.

In particular, when the rescuer presses the "ready" button, rather than apply a shock immediately that will cause the patient's body to jump dramatically, the resuscitation control box will thank the rescuer and instruct the rescuer to remain clear of the patient and then wait for about two seconds (the resuscitation control box may describe this period to the rescuer as being an internal safety check, even if no substantial safety check is being performed). This process has an effect similar to a conversation that hands responsibility to the resuscitation control box, which makes the decision whether to apply the shock. Thus, the system maintains the rescuer safety features of a semi-automatic external defibrillator, because the rescuer must press the "ready" button before each shock, while appearing to operate more as a fully automatic external defibrillator because the time delay immediately prior to each shock leaves the rescuer with the impression that operation of the equipment is out of the hands of the rescuer. The use of CPR prompts in combination with the defibrillation also adds to the sense that the rescuer is simply following instructions from the resuscitation control box.

With reference to FIGS. 6-9, when the rescuer turns the resuscitation control box on (step 101), the resuscitation control box first informs the rescuer that the rescuer can temporarily halt prompting by pressing the PAUSE button (step 102), and then, after a pause, instructs the rescuer to check responsiveness of patient, and if the patient is non-responsive to call an emergency medical service (EMS) (steps 103, 104). The resuscitation control box then instructs the rescuer to check the patient's airway to determine whether the patient is breathing (steps 105-107).

After a pause, the resuscitation control box then instructs the rescuer that if the patient is breathing the patient should be placed on the patient's side, unless trauma is suspected, and that the rescuer should press the PAUSE button (steps 108-109). Then the resuscitation control box instructs the rescuer to perform mouth-to-mouth resuscitation if the patient is not breathing (steps 110-114). Then the resuscitation control box instructs the rescuer to press an Airway Help button A if the patient's airway is blocked, so that the resuscitation control box can give prompts for clearing obstructed airways (steps 115 of FIG. 6B and 147-158 of FIGS. 9A-9B).

Next, after a pause (step 116a), if the resuscitation control box does not include pulse oximetry or phonocardiogram capability (step 116b), the resuscitation control box instructs the rescuer to check the patient's pulse (step 117). After another pause, the resuscitation control box instructs the rescuer to press a Breathing Help button B if the patient's pulse is okay but the patient is not breathing, so that the resuscitation control box can give prompts for assisting the patient's breathing (steps 118 and 119 of FIG. 7A and 140-146 of FIG. 8). Light-emitting diodes adjacent the various buttons indicate which button has been pressed most recently (only one light remains on at a time). The resuscitation control box next prompts the rescuer to contact an emergency medical system (step 120) and to open the patient's shirt or blouse and attach the adhesive pads (steps 122f-122h).

If the resuscitation control box does include pulse oximetry or phonocardiogram capability (step and 116b), the resuscitation control box prompts the rescuer to open the patient's shirt or blouse and attach the adhesive pads (steps 121 and 122a). If the pulse oximetry or phonocardiogram system does not provide a valid pulsatile reading (step 122b), then the flow chart proceeds to step 117. If the pulse oximetry or phonocardiogram system does provide a valid pulsatile reading and detects a pulse (steps 122b and 122c), then the resuscitation control box begins the breathing help routine (steps 122d of FIG. 7B and step 140 of FIG. 8). If the pulse oximetry or phonocardiogram system does not detect a pulse, then the resuscitation control prompts the rescuer to contact an emergency medical system (step 122e), measures the impedance of the patient to determine whether it is within an acceptable range for application of shocks (step 123) and determines whether the patient's rhythm is shockable (steps 124). If the rhythm is shockable, the resuscitation control box causes a sequence of shocks to be applied to the patient, each shock requiring the rescuer first to press the "READY" button on the resuscitation control box (steps 124-131). After the last shock in the sequence, or if the rhythm is non-shockable, the resuscitation control box prompts the rescuer in CPR (steps 132-139). The flowchart then returns to step 117.

Figure 8:
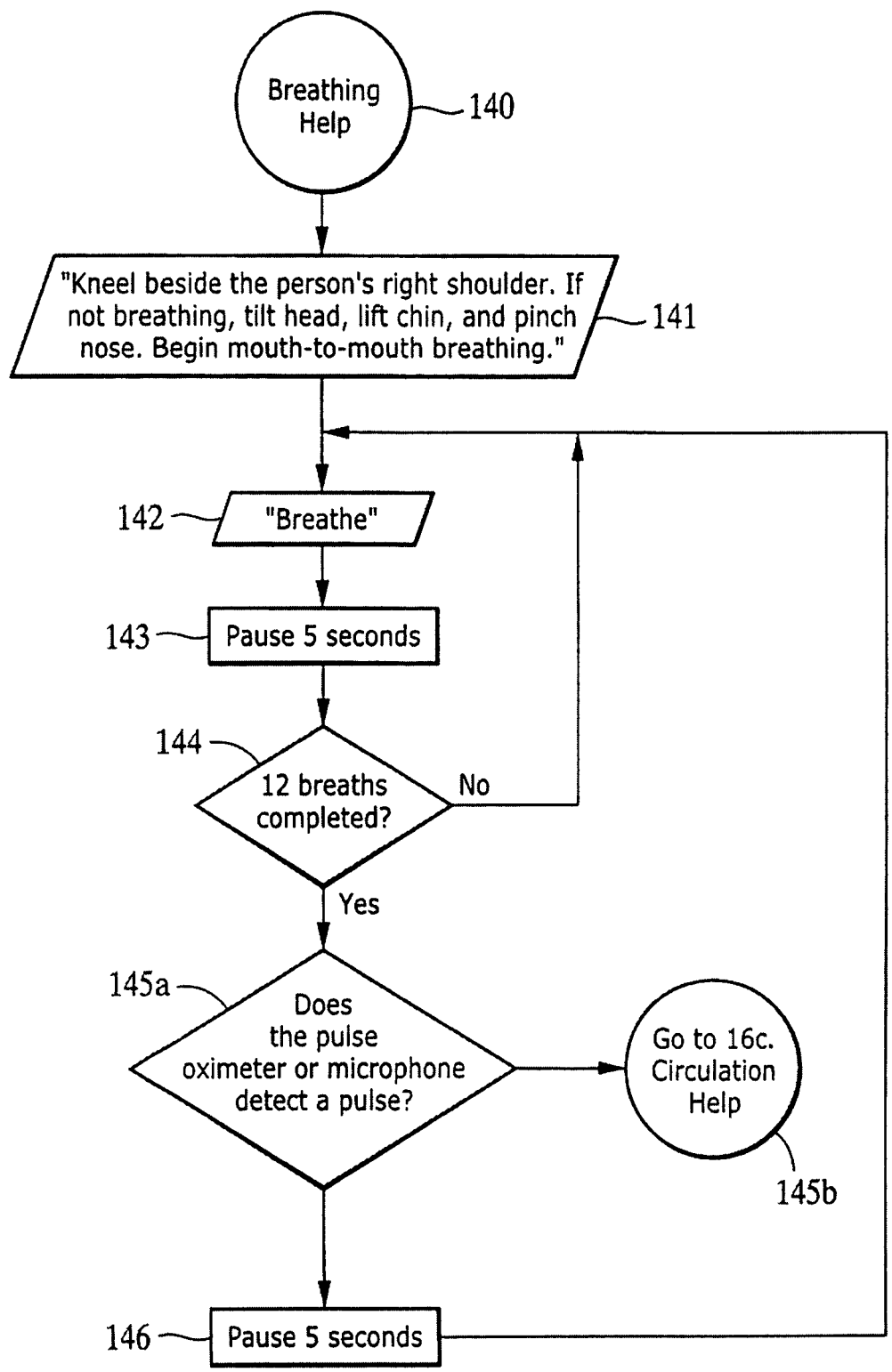
FIG. 8 is a flowchart illustrating the "breathing help" routine of the resuscitation system.
Figure 9A:
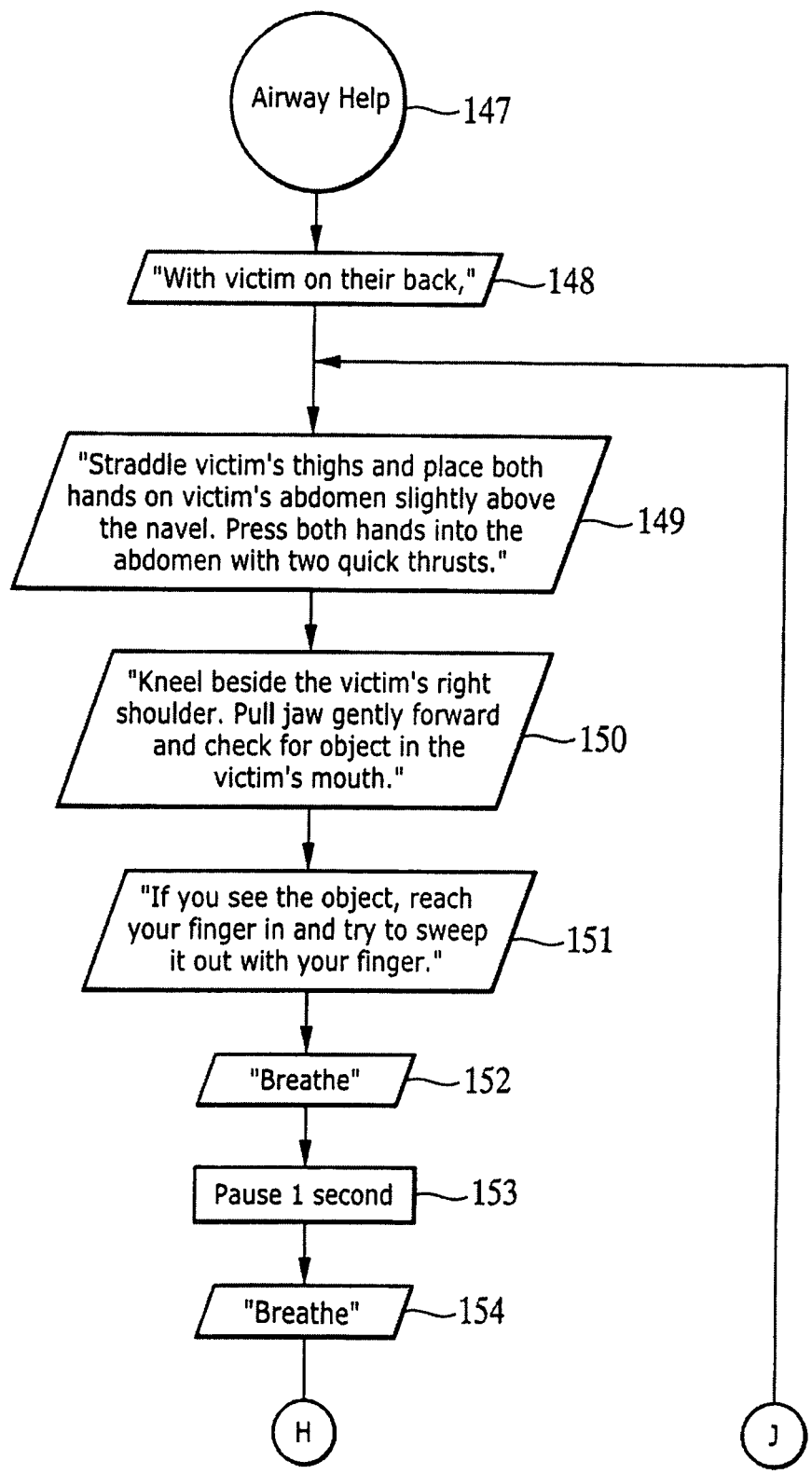
FIGS. 9A and 9B are a flowchart illustrating the "airway help" routine of the resuscitation system.
Figure 9B:
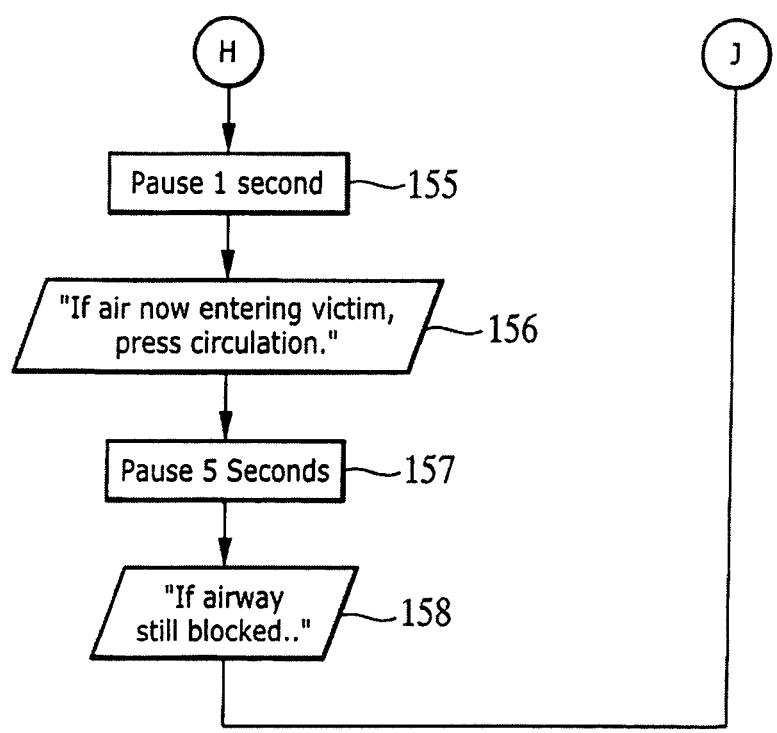
Figure 10:
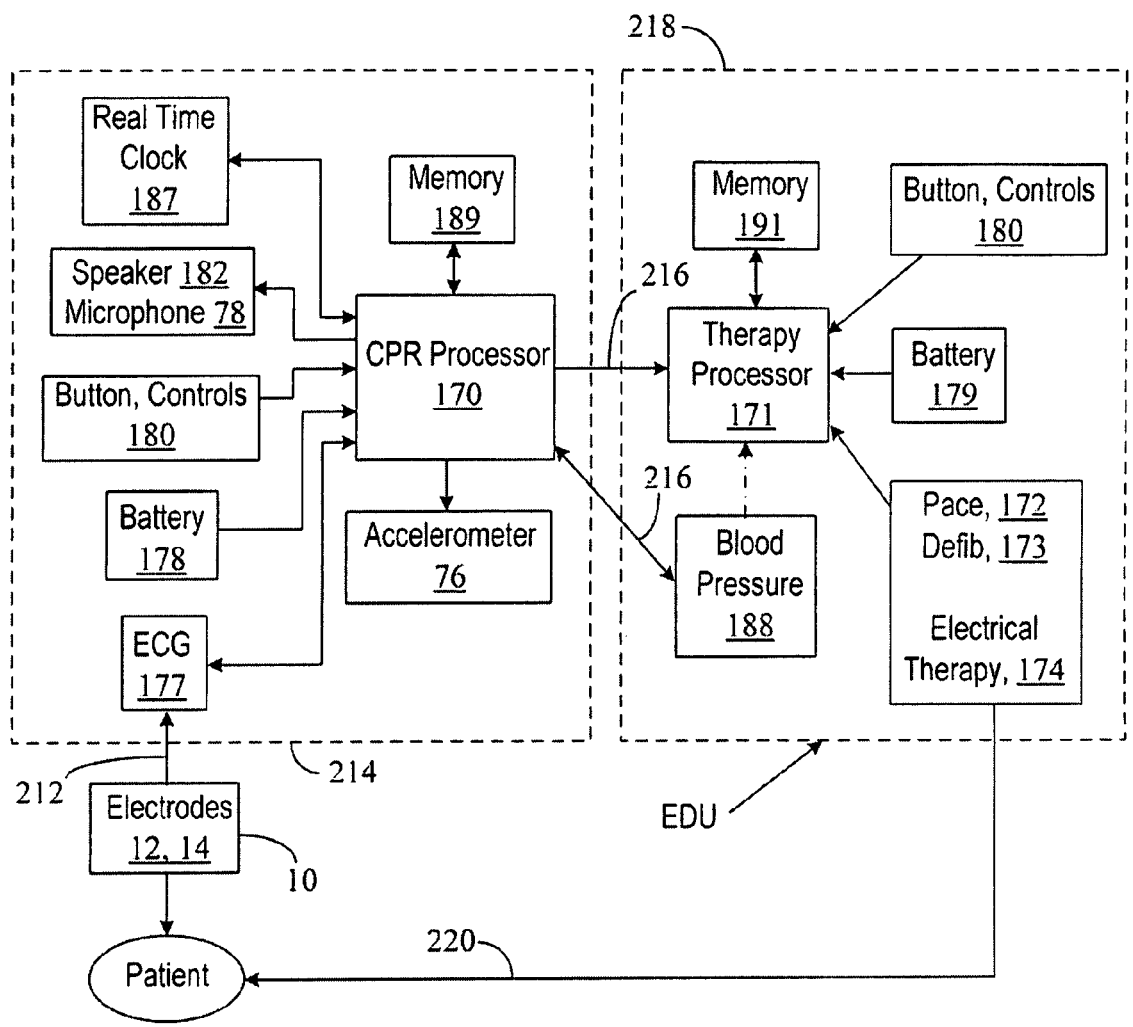
FIG. 10 is a block diagram of the electronic circuitry of an alternative implementation.
Figure 11:
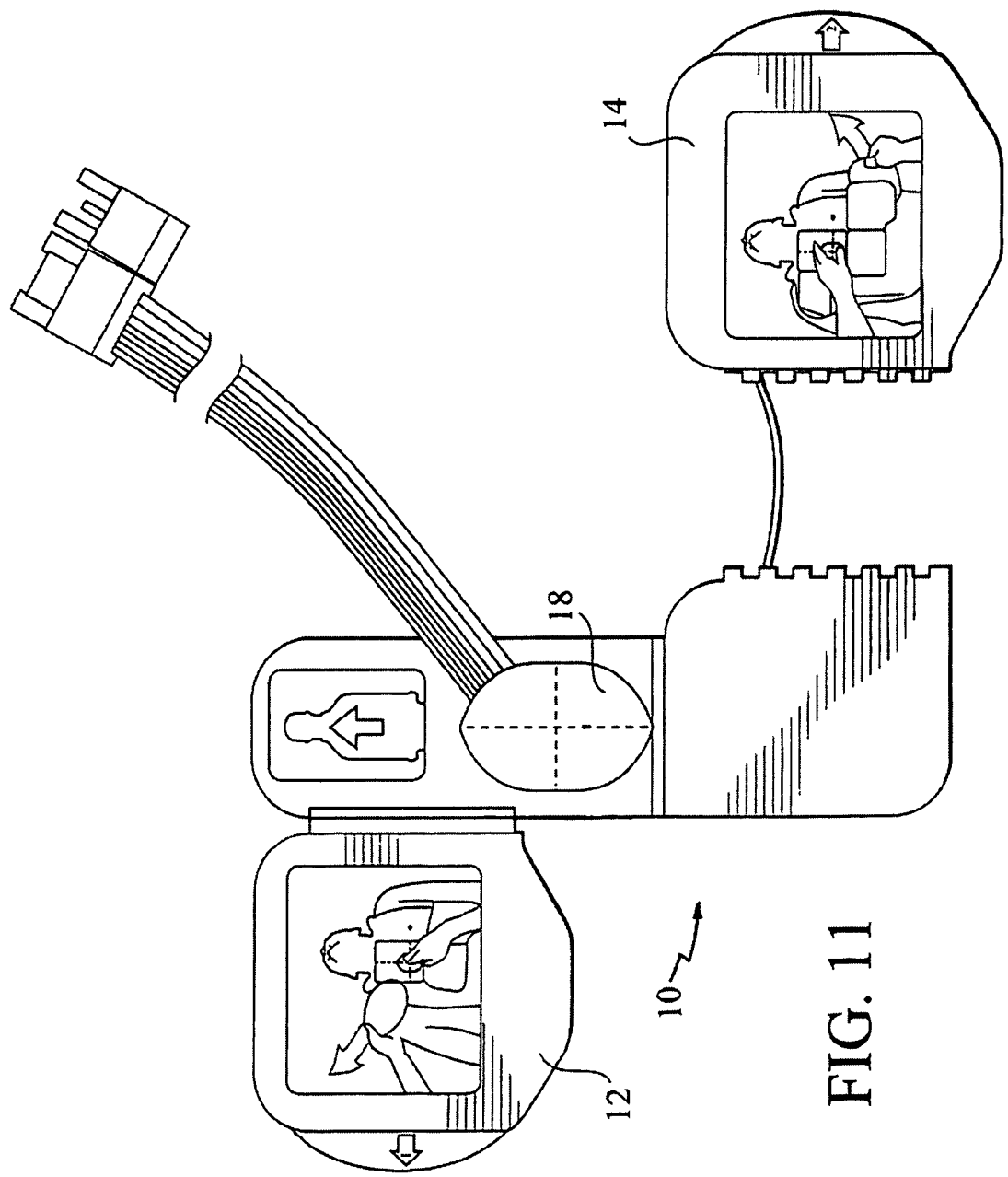
FIG. 11 is a drawing of the defibrillation electrode assembly of another alternative.

FIG. 8 shows die steps 140-146 for prompting the rescuer to assist the patient's breathing. After 12 breaths have been completed (step 144), the pulse oximetry or phonocardiogram system attempts to detect a pulse (step 145a), or, if the system does not include a pulse oximetry or phonocardiogram system, the resuscitation control box prompts the rescuer to check the patient's pulse. If no pulse is present, the resuscitation control box prompts the rescuer to press a Circulation Help button C (step 145b) that brings the rescuer back to the circulation portion of the flowchart. Otherwise, if a pulse is detected, then the flow chart of FIG. 8 returns to step 142.

The combined defibrillation and CPR resuscitation assembly provided can be less intimidating than conventional AEDs because the assembly is not devoted solely to defibrillation. Moreover, the resuscitation assembly is less intimidating because it accommodates common skill retention problems with respect to necessary techniques ancillary to defibrillation such as mouth-to-mouth resuscitation and CPR, including the appropriate rates of chest compression, the proper location for performing compressions, the proper manner of tilting the patient's head. In addition, because the rescuer knows that it may never even be necessary to apply a defibrillation shock during use of the resuscitation assembly, the rescuer may be more comfortable using the resuscitation assembly for mouth-to-mouth resuscitation and CPR. Unlike previous CPR prompting devices, the rescuer would be required to place the electrode assembly on top of the patient, but the rescuer would do this with the belief that the resuscitation assembly will be sensing the patient's condition and that the likelihood that the resuscitation assembly is actually going to apply a shock is low. If, during this resuscitation process, the resuscitation control box instructs the rescuer to press the "READY" button so that a defibrillation shock can be applied, the rescuer will likely feel comfortable allowing the shock to be applied to the patient. Basically, the resuscitation assembly simply tells the rescuer what to do, and by that point, given that the rescuer is already using the assembly, the rescuer is likely simply to do what the rescuer is told to do. Essentially, the rescuer will be likely to view the resuscitation assembly as simply being a sophisticated CPR prompting device with an additional feature incorporated into it, and since rescuers are less likely to be intimidated by CPR prompting devices than AEDs, they will be likely to use the resuscitation assembly when it is needed.

Figure 12A:
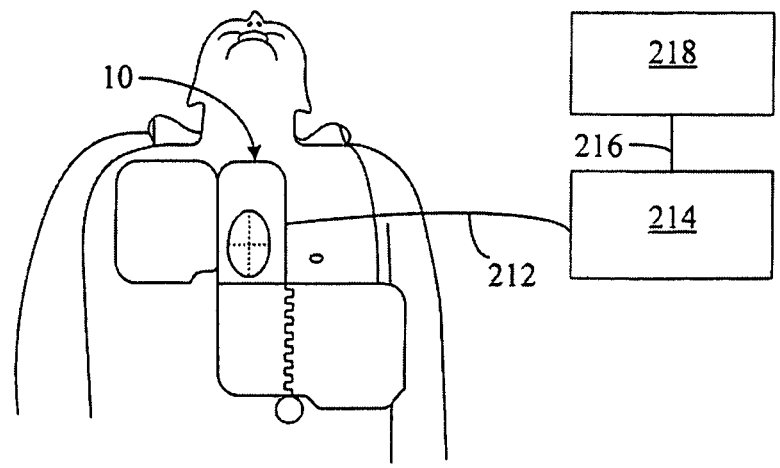
FIGS. 12A-12C are diagrammatic views of three possible implementations of first and second units.
Figure 12B:
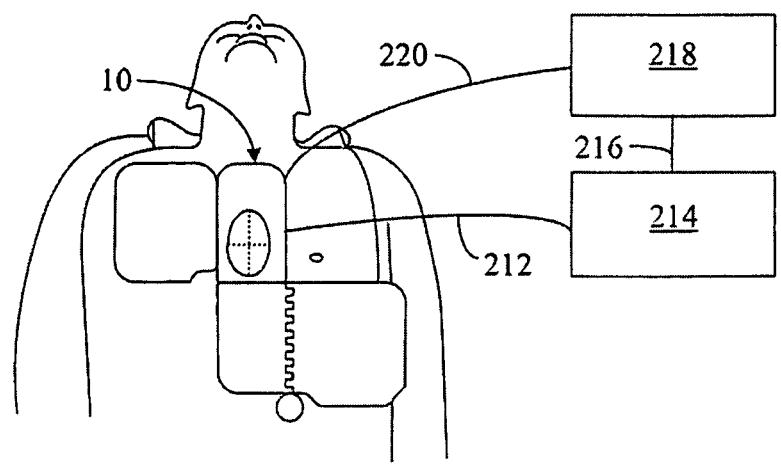
Figure 12C:
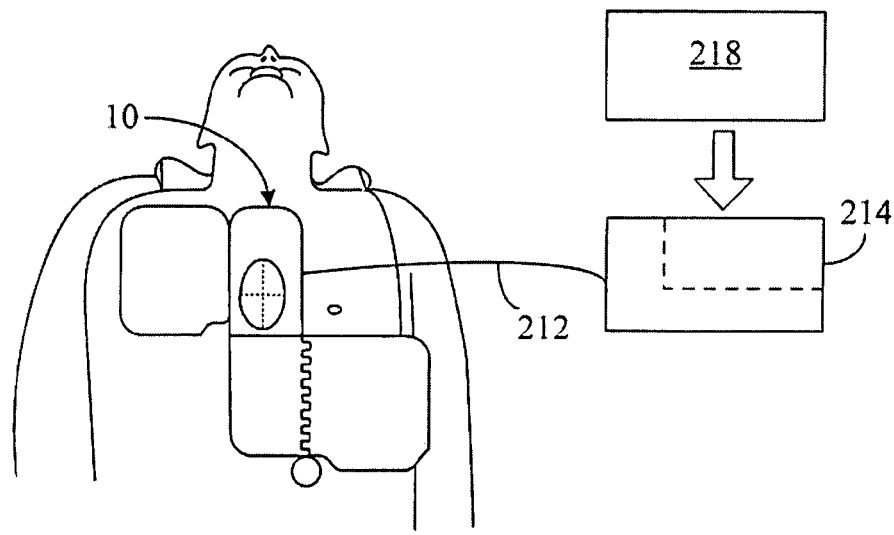

FIGS. 10, 11, and 12A-12C show alternative implementations in which an electrode pad assembly 10 is connected by a cable 212 to a first unit 214 containing the electronics for CPR prompting and resuscitation control. Another cable 216 connects the first unit to a second unit 218 containing the electronics for defibrillation and pacing therapy. A third cable 220 could be provided for making a direct connection from the second unit to the electrodes (FIG. 12B). The first unit 214 could be configured to receive the second unit 218 as an inserted module (FIG. 12C), in which case the electrical connection between the units are made internally without the use of cable 216. The primary function of the first unit 214 is to provide processing and control for CPR functions such as CPR prompts. The primary function of the second unit 218 is to provide processing and control of electrical therapy functions. The first unit includes a CPR processor 170, a battery 178, ECG circuitry 177 for amplifying and filtering the ECG signal obtained from the defibrillation pads 12, 14, a microphone 78 for recording the rescuer's voice as well as ambient sounds, an accelerometer 76, a real time clock 187, and a speaker 182 for delivering prompts to the rescuer. The second unit includes a therapy processor 171, a battery 179, buttons and controls 180, and memory 191.

The first unit could also be incorporated into the electrode pad assembly rather than being a separate box. The electronics could be provided on the rigid substrate 40 of the electrode pad assembly (FIG. 1).

Separate batteries 178, 179 and controls 180, 181 may be provided for the first (CPR) and second (therapy) units, thereby allowing the electronics in the first unit to provide CPR prompting to the operator without the need for the second unit. The cable 216 that connects the first and second units may be detachable. Memory 189 is provided in the first unit for storing information such as voice recording, ECG data, chest compression data, or electronic system status such as device failures that occur during daily self checks of the electronics initiated by a real time clock circuit.

The defibrillation electrode pad assembly 10 may incorporate defibrillation electrodes composed of a material that can be held against a patient's skin for extended periods of time (e.g., up to 30 days).

Figure 13A:
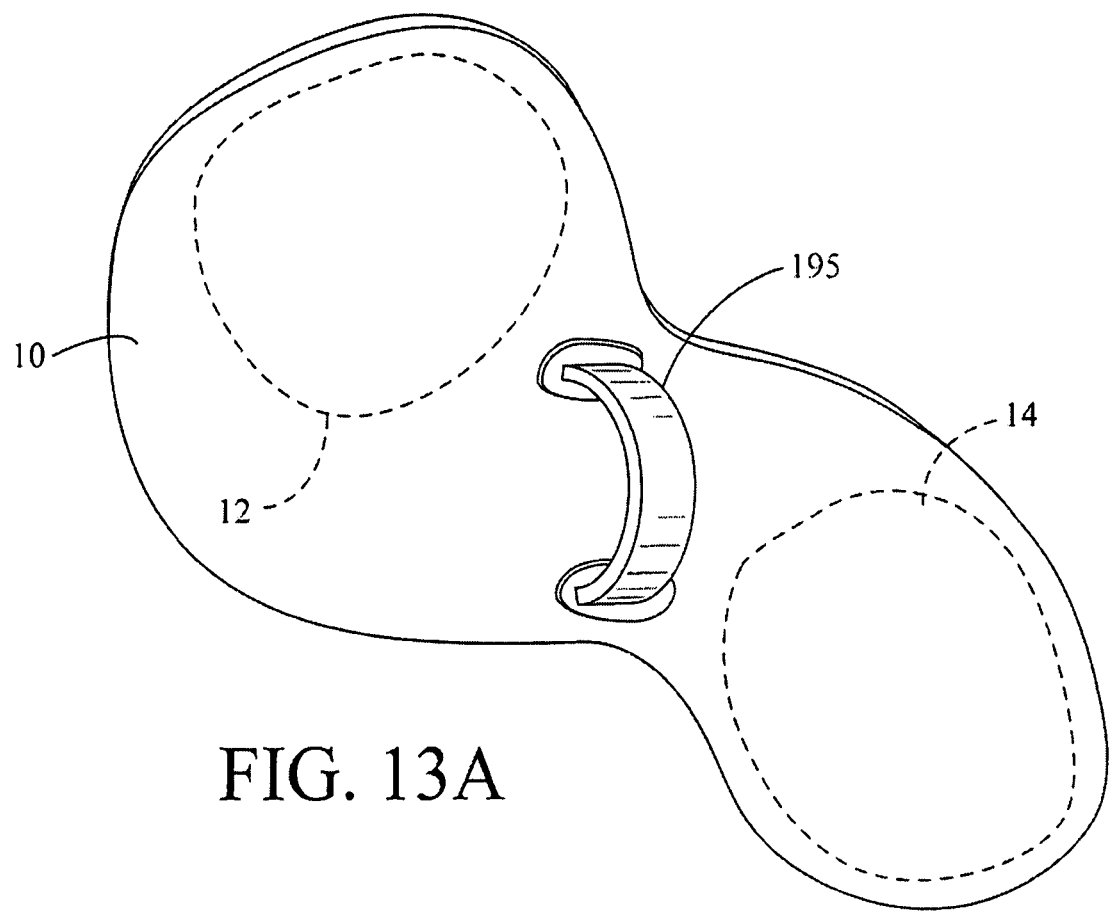
FIGS. 13A and 13B are drawings of two alternative implementations of the electrode pad assembly in which a handle is provided for the rescuer.
Figure 13B:
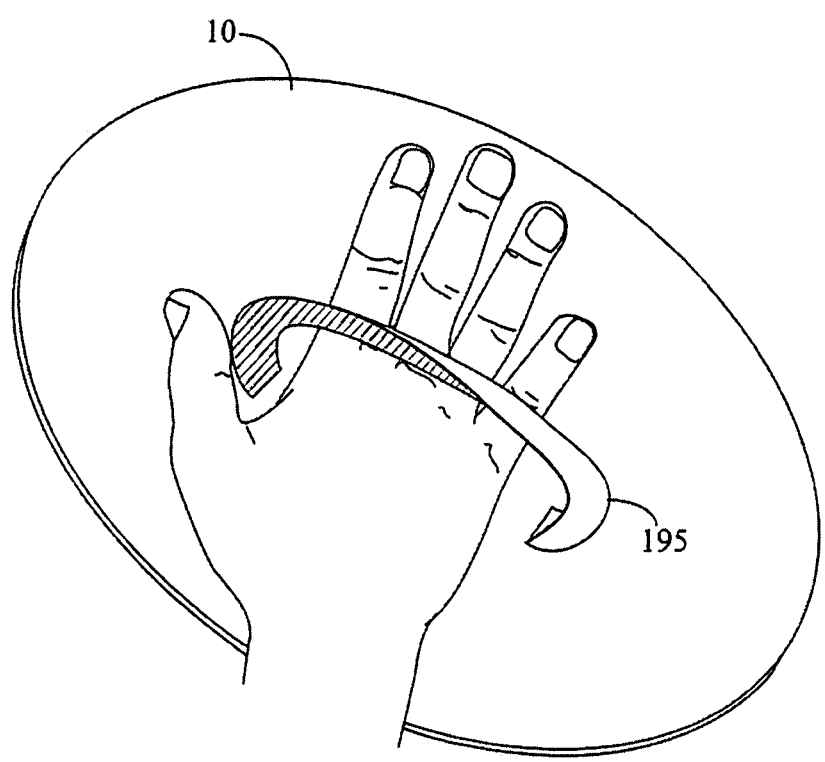

As shown in FIGS. 13A and 13B, the pad assembly 10 may also incorporate features on its upper surface facing the rescuer that provide a handle 195 for the rescuer during performance of CPR. The handle could take the form of a fabric loop (FIG. 13B) or a more rigid polymer member (FIG. 13A). The fabric could be sewn or adhered by adhesive or ultrasonic bonding to the pad 10 (FIG. 13B). The polymer handle could also be bonded by adhesive or ultrasonic bonding to the pad (FIG. 13A). It has been shown in studies that the maintenance of pressure on the chest during the decompression phase of chest compression results in a significant decrease in the effectiveness of the chest compressions. The handle 195 motivates the rescuer to pull up at least slighltly during the decompression phase. The adhesive gel of the electrode pad, or other adhesive, can extend under the region where the rescuer's hands are placed during compression thus providing adhesion of the pad to the skin while the rescuer pulls on the handle during the decompression phase. Pulling up on the chest during the decompression phase has been shown to heighten negative intrathoracic pressure, increasing venous return and thus increasing blood flow during chest compressions.

In another implementation, the first unit may be adapted to be supported by the patient for long periods of time. The unit could be incorporated into the electrode pad assembly as suggested above, or it could be a separate unit configured to be worn by the patient. In such an implementation, the electronics of the first unit are designed to allow for long term monitoring of the patient's condition via die ECG 177 and physiological monitoring 176 circuitry. If a physiological condition is detected that is deemed hazardous to the patient by the CPR processor 170, based on analysis of the ECG and other physiological parameters, an alarm is sounded to the patient via the speaker 182.

An activity sensor and associated circuitry can inform the CPR processor of whether the patient is moving. For example, accelerometer 76 could serve as the activity sensor, and detect whether or not the patient is moving. Patient motion may be detected using a variety of different algorithms, including, for example the following: The acceleration signal is integrated over one-second intervals to provide an estimate of velocity. Velocity is integrated over the same one-second intervals to provide an estimate of displacement. The root means square velocity is calculated for each one-second interval. If either the RMS velocity exceeds 0.2 cm/s or the peak displacement exceeds 0.5 cm, the patient is determined to be moving.

If the algorithm determines that a cardiac emergency event is occurring, the first unit can send a message directly to a medical emergency response system, such as 911. This call be done using a variety of known communication techniques, e.g., Bluetooth, cellular phone, Ultra Wideband (UWB). If the activity sensor has determined that the patient is still moving during the cardiac emergency, the unit could also issue a prompt indicating, "Call 911 Immediately!"

The first unit will be able to determine the orientation of the patient, e.g., based on the accelerometer output. It can detect if a patient has fallen down and initiate a message to the emergency system. It can also determine whether the patient is lying on his back, the proper orientation for doing CPR. Thus, a specific prompt can be provided to the rescuer that tells them to roll the patient on their back prior to beginning CPR, should the device detect an improper orientation of the patient.

Other implementations may include signal analysis software for predicting the risk of a heart attack. When a threshold is exceeded in the value of that risk probability, a voice prompt may be provided to the patient via the speaker 182 to contact the medical emergency system. By using the motion detection capabilities of the accelerometer to measure and track a patient's activity level (PAL), and combining the activity level calculation with measurements of the ECG 177, e.g., ST-segment elevation (STE), the first unit is able to provide a predictor of the risk of an impending heart attack or cardiac arrest. An ST segment elevation exceeding a threshold such as 300 microvolts on the ECG provides an indicator of impending heart attack. In the preferred embodiment, ST segment elevation in the presence of increased physical activity is an indication of further risk of potential cardiac arrest. The calculation of risk probability may be accomplished by first performing a logistic regression of variables such as STE and PAL as predictors of cardiac arrest within 24 hours. The calculation may take the form of a linear regression equation such as $$0.24\ STE + 0.12\ PAL = RISK.$$

Alternatively, nonlinear regression may be performed to allow for a multiplicative term such as $$0.24\ STE + 0.12\ PAL + 0.54\ (STE*PAL) = RISK.$$

The multiplicative term heightens the importance of STE in the presence of PAL.

Parameters such as STE, PAL and RISK may additionally be stored in memory and multiple readings and calculations performed over time. The sequence of readings may then be analyzed for trends in the physiological state of the patient that can augment the RISK calculation taken at a single point in time. For instance, if STE is found to be steadily rising over a series of readings, the voice prompt may be triggered sooner than at a fixed threshold of 300 microvolts.

Additionally, the ECG may be analyzed to determine the interval between adjacent R-waves of the QRS complexes and using this interval to calculate heart rate variability as a running difference between adjacent R-R intervals. It is known that the R-R interval will vary following an ectopic beat or ventricular premature contraction (VPC). In a healthy heart, the R-R interval will decrease immediately following the VPC followed by a gradual return to steady state; a heart with an increased risk of heart attack will show a decreased level of variability. This effect is sometimes called heart rate turbulence. Two variables are calculated: (1) the Relative Change in R-R interval (RCRR) between pre- and post-VPB R-R intervals, $$RCRR=(R\text{-}R\text{ pre-}VPB-R\text{-}R\text{ post-}VPB)/R\text{-}R\text{ pre-}VPB$$

and (2) the slope of the change of R-R interval (SRR) while it is undergoing its post-VPB decrease. If the RCRR is non-negative and the slope SRR does not steeper than −2 ms/R-R interval then the patient is considered as at risk. Alternatively, the individual calculations may be included along with STE and PAL to create an integrated measurement vector as discussed in the preceding paragraphs. Other signal analysis algorithms may incorporate analysis of heart rate variability in the frequency domain, wavelet domain or using non-linear dynamics-based methods.

Since VPBs are often rare events, the defibrillation electrode pad 10 may include circuitry to stimulate the patient with a single pulse of low enough amplitude to cause a VPB without undue discomfort to the patient, under the patient's control. An additional control is provided on the low-profile button panel 20 so that the patient may initiate the pulse under their control. Alternatively, the device is programmed to automatically deliver the pulse at regular intervals such as at 24-hour intervals, at a time of day when the patient may conveniently have access to the device, such as in the morning. While the pulse generator 186 may be located in the second (therapy) unit, it is preferably contained as part of the first (CPR) unit.

In another implementation, the activity monitoring capability of the first unit may be utilized so that the activity state of the patient is continuously monitored. Using the activity monitoring capability and a real time clock 187, the first unit may detect when a patient has woken up in the morning. After there has been 10 minutes of regular motion detected, the unit may prompt the patient that it would like to perform a test. If the patient assents to the test indicated by a press of the TEST button on the low-profile button panel 20, the unit will send out a small current pulse, preferably a 40 millisecond pulse of 75 mA amplitude that is synchronized to the patient's ECG so that it occurs approximately 200 mS prior to the R-wave and after the T-wave so as not to introduce any arrhythmias. The pulse will safely cause a VPB in the patient which can then be used to measure the autonomic response to a VPB to provide regular calculations of the autonomic response to a VPB as measured by such parameters, though not limited to, STE and PAL, and providing a daily update to the RISK calculation.

Additional physiological measurement, preferably that of blood pressure, may be incorporated into the RISK calculation. A sudden change in systolic or mean arterial blood pressure of greater than 10-15 points is indicative of an increased risk of cardiac arrest. In the preferred embodiment, the blood pressure measurement device would be a handheld, inflated cuff blood pressure device 188. The blood pressure cuff 188 would have wireless communication capability with the CPR Processor 170 and at the conclusion of each measurement, the blood pressure reading along with a date and time stamp would be stored in memory 189 of the CPR Processor 170 for subsequent use in calculating RISK. This scheme would allow the patient to carry the small blood pressure cuff along with them during their daily activities and take blood pressure measurements at regular intervals without having to return home. Alternatively, the blood pressure measurement device may communicate with the therapy processor and may additionally get power from and be physically connected to the second (therapy) unit by a cable. The patient will then be required to take regular blood pressure readings at the second unit, typically a larger device that may or may not be portable. Communication of the blood pressure readings may be accomplished over a cable between the first (CPR) and second units (therapy) units, e.g., cable 216, or wirelessly, using such technology as Bluetooth.

The second unit 218 may in some implementations be thought of as an energy delivery unit (EDU), in which case it Would incorporate a defibrillator 172, pacer 173, or other electrical therapy 174. In some implementations, the EDU would be small and light enough to be worn in a harness or belt to be carried around continuously by the patient. The EDU 218 may in some cases not contain a therapy processor 171, but be a "dumb" device that requires the controls provided by connection to the processor in the first (CPR) unit, e.g., on the defibrillator pad 10, in order to deliver electrical therapy to the patient.

In some cases, the patient may not even own an EDU due to the significant costs inherent in the high-voltage components necessary. The patient would only own the first unit and defibrillator pad, as the components incorporated in them are less expensive, e.g., they can be manufactured from less-expensive, consumer-type electronics. In such a case, when the patient did not own the EDU, and had a heart attack, a bystander or family member who encountered the cardiac arrest victim would be prompted to begin CPR. It has been shown now in several studies that performing good CPR for extended periods prior to delivery of a shock are not only not detrimental to long term survival, but in fact increase survival rates. CPR would thus begin with built-in prompting and when the paramedic arrives with the defibrillator it can be connected to the pads to deliver the electrical therapy. If the first (CPR) unit is separate from the electrode pad assembly, the EDU connection to the electrodes could be direct, or via a cable connected to the first (CPR) unit. If the defibrillator is an EDU or other compatible device, patient and performance data stored by the first (CPR) unit may be downloaded to the defibrillator.

Many other implementations of the invention other than those described above are within the invention, which is defined by the following claims. For example, the defibrillation pads 10, 12 may be separable from the CPR-prompting first unit and be connected at the time that the EDU is brought to the scene; the defibrillation pads may be connected both electrically and mechanically to the CPR-prompting first unit at that time. A greater amount of the control functionality may be put into the first unit, leaving essentially only the circuitry for providing the defibrillation pulses in the second unit. The first unit may be incorporated into the defibrillation electrode pad assembly, or made a separate unit connected to the pad assembly by one or more cables. The second unit may connect to the first unit by one or more cables, or by a wireless connection. The defibrillation pulses may pass through the first unit (FIG. 12A), or be routed directly to the defibrillation electrodes via one or more cables running from the second unit to the electrodes (FIG. 12B). The second unit may connect to the first unit by being plugged into the first unit (FIG. 12C), without the need for a cable (e.g., the second unit could be a defibrillation module that plugs into the first unit).

In some implementations the second (therapy) unit can provide pacing therapy as well as defibrillation therapy. Pulse detection methods other than pulse oximetry and phonocardiogram may be employed. Any method capable of detecting a victim's pulse can be used for pulse detection.

What is claimed is:

1. A resuscitation system for use by a rescuer for resuscitating a patient, comprising:
    at least two high-voltage defibrillation electrodes;
    a first electrical unit comprising circuitry for monitoring at least an ECG signal;
    a second electrical unit mechanically separate from the first unit and comprising circuitry for providing defibrillation pulses to the electrodes; and
    at least one detachable electrical connection between the electrodes and the second unit for transmitting the defibrillation pulses to the electrodes;
    wherein the two electrodes and the first unit are configured to be worn by the patient while the patient is moving;
    wherein the second unit is configured to be electrically attached to the electrodes during some periods of time, and electrically detached during other periods; and
    wherein the at least two high-voltage defibrillation electrodes are adapted to be worn by the patient for extended periods of time.

2. The resuscitation system of claim 1 wherein the second unit is configured to be mechanically detachable from the first unit when the second unit is electrically detached from the electrodes.

3. The resuscitation system of claim 1 wherein the first unit is separate from the two electrodes, and connected to the two electrodes by one or more cables.

4. The resuscitation system of claim 1 wherein the first unit is capable of providing resuscitation prompts without being electrically connected to the second unit.

5. The resuscitation system of claim 4 wherein the first unit comprises a source of electrical power and a processor.

6. The resuscitation system of claim 4 wherein the first unit comprises a speaker for providing the resuscitation prompts.

7. The resuscitation system of claim 4 wherein the resuscitation prompts comprise spoken and visual prompts.

8. The resuscitation system of claim 1 wherein the resuscitation prompts comprise CPR prompts.

9. The resuscitation system of claim 1 wherein the circuitry for providing at least one detachable electrical connection between the electrodes and second unit comprises at least one cable providing a direct electrical connection to the electrodes.

10. The resuscitation system of claim 1 wherein the at least one detachable electrical connection comprises one or more cables that carry the defibrillation pulses to the electrodes.

11. The resuscitation system of claim 1 wherein the first unit comprises a microphone and circuitry for storing sounds recorded during use of the unit.

12. The resuscitation system of claim 1 wherein the second unit is configured to be supported on the patient when electrically attached.

13. The resuscitation system of claim 1 wherein the second unit delivers defibrillation pulses to the electrodes via an electrical connection from the second unit to the first unit, and the first unit delivers the defibrillation pulses to the electrodes via an electrical connection from the first unit to the electrodes, and wherein the connection from the second unit to the first unit forms at least a portion of the detachable electrical connection.

14. The resuscitation system of claim 12 wherein the second unit is supported on the patient by being mechanically connected to the first unit.

15. The resuscitation system of claim 14 wherein the mechanical and electrical connection of the second unit to the first unit is achieved by inserting at least a portion of the second unit into at least a portion of the first unit.

16. The resuscitation system of claim 1 wherein the second unit is mechanically connectable to the first unit.

17. The resuscitation system of claim 1, wherein the at least two high-voltage defibrillation electrodes are part of an electrode assembly.

18. The resuscitation system of claim 1 wherein the patient's ECG is detected through ECG-detecting electrodes in electrical contact with the patient.

19. The resuscitation system of claim 18 wherein the ECG-detecting electrodes comprise at least portions of one or more electrode assemblies that deliver the high voltage defibrillation pulses.

20. The resuscitation system of claim 19 wherein the ECG-detecting electrodes comprise substantially the same electrodes as used to deliver the high voltage defibrillation pulses.

* * * * *

UNITED STATES PATENT AND TRADEMARK OFFICE
CERTIFICATE OF CORRECTION

PATENT NO. : 9,782,123 B2  
APPLICATION NO. : 11/928087  
DATED : October 10, 2017  
INVENTOR(S) : Gary A. Freeman and Mark Totman Page 1 of 1

It is certified that error appears in the above-identified patent and that said Letters Patent is hereby corrected as shown below:

In the Claims

In Claim 8, Column 18, Line 1, please delete "claim 1", and insert --claim 4--.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*